(12) United States Patent
Osborne

(10) Patent No.: US 10,130,577 B2
(45) Date of Patent: *Nov. 20, 2018

(54) PERSONAL CARE COMPOSITIONS

(71) Applicant: The Procter & Gamble Company, Cincinnati, OH (US)

(72) Inventor: Rosemarie Osborne, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 14 days.

This patent is subject to a terminal disclaimer.

(21) Appl. No.: 15/448,791

(22) Filed: Mar. 3, 2017

(65) Prior Publication Data
US 2017/0172886 A1  Jun. 22, 2017

Related U.S. Application Data

(60) Division of application No. 14/494,742, filed on Sep. 24, 2014, now Pat. No. 9,616,011, which is a continuation of application No. 13/082,285, filed on Apr. 7, 2011, now Pat. No. 8,871,717, which is a division of application No. 11/411,285, filed on Apr. 26, 2006.

(60) Provisional application No. 60/675,264, filed on Apr. 27, 2005.

(51) Int. Cl.
| | |
|---|---|
| A61K 38/00 | (2006.01) |
| A61K 8/64 | (2006.01) |
| A61Q 19/00 | (2006.01) |
| A61Q 5/12 | (2006.01) |
| A61Q 5/00 | (2006.01) |
| A61K 8/04 | (2006.01) |
| A61K 8/06 | (2006.01) |
| A61K 8/29 | (2006.01) |
| A61K 8/34 | (2006.01) |
| A61K 8/37 | (2006.01) |
| A61K 8/41 | (2006.01) |
| A61K 8/49 | (2006.01) |
| A61K 8/60 | (2006.01) |
| A61K 8/63 | (2006.01) |
| A61K 8/67 | (2006.01) |
| A61K 8/891 | (2006.01) |
| A61K 8/97 | (2017.01) |
| A61Q 17/04 | (2006.01) |
| A61Q 19/02 | (2006.01) |
| A61Q 5/02 | (2006.01) |

(52) U.S. Cl.
CPC .............. *A61K 8/64* (2013.01); *A61K 8/046* (2013.01); *A61K 8/062* (2013.01); *A61K 8/064* (2013.01); *A61K 8/29* (2013.01); *A61K 8/347* (2013.01); *A61K 8/37* (2013.01); *A61K 8/41* (2013.01); *A61K 8/498* (2013.01); *A61K 8/60* (2013.01); *A61K 8/63* (2013.01); *A61K 8/67* (2013.01); *A61K 8/675* (2013.01); *A61K 8/676* (2013.01); *A61K 8/678* (2013.01); *A61K 8/891* (2013.01); *A61K 8/97* (2013.01); *A61Q 5/00* (2013.01); *A61Q 5/006* (2013.01); *A61Q 5/12* (2013.01); *A61Q 19/00* (2013.01); *A61K 2800/10* (2013.01); *A61K 2800/5922* (2013.01); *A61Q 5/02* (2013.01); *A61Q 17/04* (2013.01); *A61Q 19/02* (2013.01)

(58) Field of Classification Search
CPC ..... A61K 38/00; A61K 2800/10; A61K 38/05
See application file for complete search history.

(56) References Cited

U.S. PATENT DOCUMENTS

| | | |
|---|---|---|
| 1,985,424 A | 12/1934 | Piggott |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,703,798 A | 3/1955 | Schwartz |
| 2,809,971 A | 10/1957 | Bernstein et al. |
| 2,826,551 A | 3/1958 | Geen |
| 2,965,576 A | 12/1960 | Wilson |
| 3,152,046 A | 10/1964 | Kapral |
| 3,155,591 A | 11/1964 | Hilfer |
| 3,236,733 A | 2/1966 | Karsten et al. |
| 3,332,880 A | 7/1967 | Kessler et al. |
| 3,753,196 A | 8/1973 | Kurtz et al. |
| 3,755,560 A | 8/1973 | Dickert et al. |

(Continued)

FOREIGN PATENT DOCUMENTS

| | | |
|---|---|---|
| CA | 2 465 123 A1 | 5/2003 |
| EP | 228868 A2 | 7/1987 |

(Continued)

OTHER PUBLICATIONS

International Search Report, PCT/US2006/016418, dated Sep. 29, 2006 (7 pages).

(Continued)

*Primary Examiner* — Marcela M Cordero Garcia
*Assistant Examiner* — Jia-Hai Lee
(74) *Attorney, Agent, or Firm* — John G. Powell

(57) ABSTRACT

Personal care compositions comprising a dipeptide and methods of using such compositions to treat the condition of keratinous tissue. The C terminal amino acid of said dipeptide is threonine. The personal care composition can be applied topically, ingested orally, injected, or used as part of a combined treatment regimen.

14 Claims, No Drawings

Specification includes a Sequence Listing.

(56) References Cited

U.S. PATENT DOCUMENTS

| | | | |
|---|---|---|---|
| 3,761,418 | A | 9/1973 | Parran, Jr. |
| 3,929,678 | A | 12/1975 | Laughlin et al. |
| 3,958,581 | A | 5/1976 | Abegg et al. |
| 3,959,461 | A | 5/1976 | Bailey et al. |
| 3,962,418 | A | 6/1976 | Birkofer |
| 3,964,500 | A | 6/1976 | Drakoff |
| 4,089,945 | A | 5/1978 | Brinkman et al. |
| 4,152,416 | A | 5/1979 | Spitzer et al. |
| 4,197,865 | A | 4/1980 | Jacquet et al. |
| 4,217,914 | A | 8/1980 | Jacquet et al. |
| 4,323,683 | A | 4/1982 | Bolich, Jr. et al. |
| 4,345,080 | A | 8/1982 | Bolich, Jr. |
| 4,364,837 | A | 12/1982 | Pader |
| 4,379,753 | A | 4/1983 | Bolich, Jr. |
| 4,381,919 | A | 5/1983 | Jacquet et al. |
| 4,387,090 | A | 6/1983 | Bolich, Jr. |
| 4,421,769 | A | 12/1983 | Dixon et al. |
| 4,422,853 | A | 12/1983 | Jacquet et al. |
| 4,470,982 | A | 9/1984 | Winkler |
| 4,507,280 | A | 3/1985 | Pohl et al. |
| 4,529,586 | A | 7/1985 | De Marco et al. |
| 4,557,853 | A | 12/1985 | Collins |
| 4,599,379 | A | 7/1986 | Flesher et al. |
| 4,628,078 | A | 12/1986 | Glover et al. |
| 4,663,158 | A | 5/1987 | Wolfram et al. |
| 4,677,120 | A | 6/1987 | Parish et al. |
| 4,741,855 | A | 5/1988 | Grote et al. |
| 4,800,197 | A | 1/1989 | Kowcz et al. |
| 4,835,148 | A | 5/1989 | Barford et al. |
| 4,835,206 | A | 5/1989 | Farrar et al. |
| 4,849,484 | A | 7/1989 | Heard |
| 4,885,107 | A | 12/1989 | Wetzel |
| 4,885,311 | A | 12/1989 | Parish et al. |
| 4,960,764 | A | 10/1990 | Figueroa, Jr. et al. |
| 4,976,953 | A | 12/1990 | Orr et al. |
| 5,011,681 | A | 4/1991 | Ciotti et al. |
| 5,049,584 | A | 9/1991 | Purcell et al. |
| 5,073,371 | A | 12/1991 | Turner et al. |
| 5,073,372 | A | 12/1991 | Turner et al. |
| 5,100,660 | A | 3/1992 | Hawe et al. |
| 5,104,646 | A | 4/1992 | Bolich, Jr. et al. |
| 5,106,609 | A | 4/1992 | Bolich, Jr. et al. |
| 5,120,532 | A | 6/1992 | Wells et al. |
| 5,124,356 | A | 6/1992 | Purcell et al. |
| RE34,075 | E | 9/1992 | Purcell et al. |
| 5,143,722 | A | 9/1992 | Hollenberg et al. |
| 5,151,209 | A | 9/1992 | McCall et al. |
| 5,151,210 | A | 9/1992 | Steuri et al. |
| 5,157,020 | A | 10/1992 | Kay et al. |
| RE34,584 | E | 4/1994 | Grote et al. |
| 5,487,884 | A | 1/1996 | Bissett et al. |
| 5,607,980 | A | 3/1997 | McAtee et al. |
| 5,652,228 | A | 7/1997 | Bissett |
| 5,674,478 | A | 10/1997 | Dodd et al. |
| 5,681,852 | A | 10/1997 | Bissett |
| 5,686,082 | A | 11/1997 | N'Guyen |
| 5,686,367 | A | 11/1997 | Hayashi |
| 5,750,122 | A | 5/1998 | Evans et al. |
| 5,821,250 | A | 10/1998 | Wu et al. |
| 5,918,590 | A | 7/1999 | Burkett |
| 5,922,758 | A | 7/1999 | Bissett |
| 5,939,082 | A | 8/1999 | Oblong et al. |
| 5,972,957 | A | 10/1999 | Wu et al. |
| 5,981,547 | A | 11/1999 | Wu et al. |
| 5,997,887 | A | 12/1999 | Ha et al. |
| 6,060,547 | A | 5/2000 | Canter |
| 6,126,939 | A | 10/2000 | Eisenbach-Schwartz |
| 6,159,485 | A | 12/2000 | Yu et al. |
| 6,245,342 | B1 | 6/2001 | Golz-Berner et al. |
| 6,492,326 | B1 | 12/2002 | Robinson et al. |
| 6,620,419 | B1 | 9/2003 | Lintner |
| 6,858,581 | B2 | 2/2005 | Kuhner |
| 7,977,308 | B2 | 7/2011 | Lintner |
| 8,871,717 | B2 | 10/2014 | Osborne |
| 2002/0058608 | A1 | 5/2002 | Cormier et al. |
| 2002/0182237 | A1 | 12/2002 | Bissett |
| 2003/0190337 | A1 | 10/2003 | Bissett |
| 2004/0063628 | A1 | 4/2004 | Piccariello et al. |
| 2004/0141939 | A1 | 7/2004 | Dal Farra et al. |
| 2004/0176273 | A1 | 9/2004 | Bissett |
| 2005/0065090 | A1 | 3/2005 | Ludin et al. |
| 2006/0239952 | A1 | 10/2006 | Hattori |
| 2007/0020220 | A1 | 1/2007 | Osborne |
| 2007/0099842 | A1 | 5/2007 | Ziegler |
| 2008/0095732 | A1 | 4/2008 | Osborne |
| 2009/0029926 | A1 | 1/2009 | Lintner |

FOREIGN PATENT DOCUMENTS

| | | | |
|---|---|---|---|
| EP | 330369 A1 | 8/1989 | |
| EP | 0505108 A1 | 9/1992 | |
| GB | 809060 | 2/1959 | |
| GB | 849433 | 9/1960 | |
| GB | 2274585 A | 8/1994 | |
| JP | 07330572 A2 | 12/1995 | |
| JP | 09012432 A2 | 1/1997 | |
| JP | 2003 344416 | 12/2003 | |
| WO | WO-86/04334 A | 7/1986 | |
| WO | WO-93/23028 A1 | 11/1993 | |
| WO | WO-96/33689 A1 | 10/1996 | |
| WO | WO-97/01313 A2 | 1/1997 | |
| WO | WO-97/21423 A1 | 6/1997 | |
| WO | WO-98/09985 A2 | 3/1998 | |
| WO | WO-01/98362 A2 | 12/2001 | |
| WO | WO-02/076423 A2 | 10/2002 | |
| WO | WO2002076423 A2 * | 10/2002 | ............... A61K 7/48 |
| WO | WO-2004/062637 A1 | 7/2004 | |
| WO | WO-2004/099237 A1 | 11/2004 | |
| WO | WO-06/114657 A1 | 11/2006 | |

OTHER PUBLICATIONS

D.G. Krzysik et al., "A New Silicone Emlsifier for Water-in-Oil Systems," Drug and Cosmetic Industry, vol. 146(4), pp. 28-81 (Apr. 1990).

Encyclopedia of Polymer Science and Engineering, vol. 15, 2d ed., pp. 204-308, John Wiley & Sons, Inc. (1989).

Falcone, J.S. "Silicones" Encyclopedia of Polymer Science and Engineering, vol. 15, 2d ed., pp. 204-308, John Wiley & Sons, Inc. (1989).

G.H. Dahms et al., "New Formulation Possibilities Offered by Silicone Copolyols," Cosmetics & Toiletries, vol. 110, pp. 91-100, Mar. 1995.

J. Smid-Korbar et al., "Efficiency and usability of silicone surfactants in emulsions," Provisional Communication, International Journal of Cosmetic Science, 12, 135-139 (1990).

M.E. Carlotti et al., "Optimization of W/O-S Emulsions and study of the Quantitative Relationships Between Ester Structure and Emulsion Properties," J. Dispersion Science and Technology, 13(3), 315-336 (1992).

Oikarinen, "The Aging of Skin: Chronoaging Versus Photoaging," Photodermatol. Photoimmunol. Photomed., vol. 7, pp. 3-4, 1990.

P. Hameyer, "Comparative Technological Investigations of Organic and Organosilicone Emulsifiers in Cosmetic Water-in-Oil Emulsion Preparations," HAPPI 28(4), pp. 88-128 (1991).

Sagarin, Cosmetics, Science and Technology, 2nd Edition, vol. 1, pp. 32-43 (1972).

Sagarin, Cosmetics, Science and Technology, 2nd Edition, vol. 1, pp. 72-73 (1972).

W. Wenner, "The Reaction of L-Ascorbic and D-Iosascorbic Acid with Nicotinic Acid and Its Amide," J. Organic Chemistry, vol. 14, 22-26 (1949).

Patent Abstract of Japan, vol. 2003, No. 12, & JP 2003 344416 A (National Institute of Advanced Industrial & Technology), Dec. 3, 2003.

Morozova et al., "Synthesis of a fragment of a polymyxin M lysine analog", Zhurnal Obshchei Khimii, vol. 37, No. 8, pp. 1764-1766, Aug. 1967.

(56) References Cited

OTHER PUBLICATIONS

Silaev, "Chemistry of polymyxin M. IV Synthesis and properties of possible fragments of polymyxin M", Zhurnal Obshchel Khitmii, vol. 31, 1961.
Kou Katayama: "A Pentapeptide From Type 1 Procollagen Promotes Extracellular Matrix Production*", Journal of Biological Chemistry, American Society of Biological Chemists, Baltimore, MD, US, vol. 268, No. 14, May 15, 1993, pp. 9941, 9944, XP000367509, ISSN: 0021-9258, figure 1.
Suetsuna and Chen, "Studies on Biologically Active Peptide Derived from Fish and Shellfish—Antioxidant Activities of Undaria pinnatifida Dipeptide Derivatives" Journal of National Fisheries University, 2002, 51 (1), pp. 1-5.
Sederma U.S. Appl. No. 11/919,539, filed Oct. 26, 2007.

* cited by examiner

US 10,130,577 B2

PERSONAL CARE COMPOSITIONS

TECHNICAL FIELD

The present invention relates to personal care compositions comprising a dipeptide and optionally one or more other ingredients. Such compositions are useful for regulating the condition of mammalian keratinous tissue (e.g., skin, hair, and/or nails).

BACKGROUND

Many personal care products currently available to consumers are directed primarily to improving the health and/or physical appearance of the skin, hair, or nails. Among these skin, hair, or nail care products, many are directed to delaying, minimizing or even eliminating skin, hair, or nail changes typically associated with the aging or the environmental damage to human skin, hair, or nails. Numerous compounds have been described in the art as being useful for regulating skin, hair, or nail condition.

Skin, hair, and nails are subject to insults by many extrinsic and intrinsic factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin, hair, or nails. Whether extrinsic or intrinsic, these factors result in visible signs of skin, hair, and nail aging and environmental damage (e.g., such as sunlight damage, smoke damage, and damage from pollutants such as nitrogen oxides, sulfur oxides, ozone, and metals such as lead). To many people, the loss of the attractiveness of skin, hair, or nails is a reminder of the disappearance of youth. As a result, the maintenance of a youthful appearance has become a booming business in youth-conscious societies. Numerous products and treatments are available in various forms to help maintain the appearance of younger hair, skin, and nails.

Extrinsic or intrinsic factors may result in the thinning and general degradation of the skin, hair, or nails. For example, as the skin, hair, and nails naturally age, there is a reduction in the cells and blood vessels that supply the skin, hair, or nails. There is also a flattening of the dermal-epidermal junction which results in weaker mechanical resistance of this junction. See, for example, Oikarinen, "The Aging of Skin: Chronoaging Versus Photoaging," Photodermatol. Photoimmunol. Photomed., vol. 7, pp. 3-4, 1990.

A large number of skin, hair, and nail care actives are known in the art and used to improve the health and/or cosmetic appearance of the skin, hair, or nails. For instance, various peptides are included in skin, hair, and nail care compositions to provide skin, hair, or nail care benefits. However, not all peptides can provide the benefits desired.

For instance, C terminal serine residues can yield dipeptides which may not be dermopharmaceutically and/or cosmetically active or which may not be useful in preferred applications. For instance, dipeptides including, for example, lysine and serine (Lys-Ser) can have inadequate properties for many dermopharmaceutical and cosmetic applications. Thus, it would be desirable to provide personal care compositions comprising a dipeptide that can provide superior properties when compared to the corresponding Lys-Ser dipeptide.

SUMMARY

The present invention provides personal care compositions comprising a dipeptide that can provide superior properties when compared to the corresponding Lys-Ser dipeptide. The dipeptide of the present invention is a dipeptide wherein the C terminal amino acid is threonine ("Thr"). More preferably, the N terminal amino acid of such dipeptide is a basic amino acid, and still more preferably one which is positively charged at a pH of 6.0. These include the naturally occurring amino acids lysine (Lys), arginine (Arg) and histidine (His). Most preferred is the use of lysine. Thus, a particularly preferred dipeptide in accordance with the present invention has the sequence Lys-Thr and N-acyl derivatives and esters, and nitrogen containing C terminal derivatives thereof.

The personal care compositions comprise one or more of such dipeptides and/or derivatives of such dipeptides, preferably in a safe and effective amount.

The present invention also relates to methods of using such compositions to regulate the condition of mammalian keratinous tissue (e.g., skin, hair, or nails). Said methods generally comprise the step of topically applying a composition of the present invention to the keratinous tissue (e.g., skin, hair, or nails) of a mammal in need of such treatment.

In another aspect, the method comprises the step of orally ingesting the dipeptide, preferably a safe and effective amount of the dipeptide, to regulate the condition of mammalian keratinous tissue (e.g., skin, hair, or nails). In one embodiment, the method comprises a dual treatment regimen comprising both oral ingestion of a composition and topical application of a composition, wherein at least one of the compositions comprises a dipeptide according to the present invention.

In another aspect, the method comprises the step of injecting the dipeptide, preferably injecting the dipeptide into and/or under the skin. In a particular embodiment, the method comprises a treatment regimen comprising a combination of injection and/or oral administration and/or topical application.

These and other features, aspects, and advantages of the present invention will become evident to those skilled in the art from a reading of the present disclosure.

DETAILED DESCRIPTION

Sequence Listing

A sequence listing that sets forth the amino acid sequences for SEQ ID NOS: 1 to 3 herein is on file as an ASCII text file titled "9970MDCDL_seq_list_ST25." This ASCII text file was created on Aug. 7, 2018 and is 4 KB in size. In accordance with MPEP § 605.08 and 37 CFR § 1.52(e), the subject matter in the ASCII text file is incorporated herein by reference.

While the specification concludes with the claims particularly pointing out and distinctly claiming the invention, it is believed that the present invention will be better understood from the following description.

As used herein, the singular term "dipeptide" is broad enough to include one or more dipeptides, dipeptide derivatives, or combinations thereof. Thus, the terms "dipeptide", "dipeptides", and "derivatives of dipeptides" are used interchangeably throughout. "Dipeptide" refers to both naturally occurring dipeptides and synthesized dipeptides, including naturally occurring and commercially available compositions that contain at least one dipeptide.

As used herein, the singular term "peptide" is broad enough to include one or more peptides, peptide derivatives, or combinations thereof. Thus, the terms "peptide", "peptides", and "derivatives of peptides" are used interchangeably throughout. "Peptide" refers to both naturally occurring peptides and synthesized peptides, including naturally occurring and commercially available compositions that contain at least one peptide.

All percentages and ratios used herein are by weight of the total composition and all measurements made are at 25° C., unless otherwise designated.

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

The terms "oral", "orally", and "oral administration", as used herein, refer to orally ingesting a composition of the present invention.

The term "dermatologically acceptable," as used herein, means that the compositions or components thereof so described are suitable for use in contact with mammalian keratinous tissue without undue toxicity, incompatibility, instability, allergic response, and the like.

The term "orally acceptable", as used herein, means that the compositions or components thereof so described are suitable for oral ingestion by a mammal without undue toxicity, incompatibility, instability, allergic response, and the like.

As used herein, "effective amount" means an amount of a compound or composition sufficient to significantly induce a positive keratinous tissue benefit, including independently or in combination with other benefits disclosed herein. This means that the content and/or concentration of dipeptide in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of dipeptide may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance or feel benefit, including independently or in combinations with the benefits disclosed herein, but low enough to avoid serious side effects, i.e., to provide a reasonable benefit to risk ratio, within the scope of sound judgment of the skilled artisan.

The personal care compositions of the present invention can be useful for treating keratinous tissue (e.g., hair, skin, or nails) condition. As use herein, "treating" or "treatment" or "treat" includes regulating and/or immediately improving keratinous tissue cosmetic appearance and/or feel. As used herein, "regulating" or "regulation" means maintaining or improving the health and/or cosmetic appearance, and includes both prophylactically regulating and/or therapeutically regulating. Regulation of keratinous tissue condition, namely mammalian and in particular human skin, hair, or nail condition, is often required due to conditions which may be induced or caused by factors internal and/or external to the body. Examples include environmental damage, radiation exposure (including ultraviolet radiation), chronological aging, menopausal status (e.g., post-menopausal changes in skin, hair, or nails), stress, diseases, disorders, etc. For instance, "regulating skin, hair, or nail condition" includes prophylactically regulating and/or therapeutically regulating skin, hair, or nail condition, and may involve one or more of the following benefits: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

As used herein, prophylactically regulating keratinous tissue condition includes delaying, minimizing and/or preventing visible and/or tactile discontinuities in keratinous tissue (e.g., texture irregularities in the skin, hair, or nails which may be detected visually or by feel), including signs of skin, hair, or nail aging. This is also encompassed within the term "treating."

As used herein, therapeutically regulating keratinous tissue condition includes ameliorating, e.g., diminishing, minimizing and/or effacing, discontinuities in keratinous tissue (e.g., skin, hair, or nails). This is also encompassed within the term "treating."

As used herein, "personal care composition" means a composition in a form intended for topical application to keratinous tissue, and/or oral ingestion, and/or injection, for the purpose of treating keratinous tissue (e.g., skin, hair, nails), and not intended for subsequent manufacture or modification.

The compositions of the present invention can also be useful for immediately improving keratinous tissue (e.g., skin, hair, or nail) cosmetic appearance and/or feel. For example, topical compositions of the present invention can be useful for regulating the cosmetic appearance of skin, hair, or nail condition by providing an immediate visual improvement in skin, hair, or nail appearance following application of the composition to the skin, hair, or nails. Generally speaking, topical compositions of the present invention which further contain particulate materials (e.g., pigments) can be most useful for providing immediate visual improvement.

The term "sagging" as used herein means the laxity, slackness, or the like condition of skin that occurs as a result of loss of, damage to, alterations to, and/or abnormalities in dermal elastin, muscle and/or subcutaneous fat.

The terms "smoothing" and "softening" as used herein mean altering the surface of the keratinous tissue such that its tactile feel is improved.

"Signs of keratinous tissue aging" include, but are not limited to, all outward visibly and tactilely perceptible manifestations as well as any other macro or micro effects due to keratinous tissue aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, fine lines, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues (e.g., fat and/or muscle), especially those proximate to the skin.

The compositions of the present invention are described in detail hereinafter.

I. Personal Care Compositions

In one aspect, the personal care compositions of the present invention comprise:

(1) a dipeptide;
(2) a dermatologically or orally acceptable carrier or an injectible liquid; and
(3) optionally, optional components.

The personal care compositions of the present invention can be in any suitable form. All forms of topical and oral personal care compositions comprising these dipeptides are contemplated and can include, for instance, creams, gels, lotions, emulsions, serums, colloids, solutions, suspensions, ointments, milks, sprays, capsules, tablets, liquids, sticks, solids, pastes, powders, compacts, pencils, spray-on formulations, brush-on formulations, cloths, wipes, and the like.

Non-limiting examples of topical personal care compositions can include, without limitation, lipstick, mascara, rouge, foundation, blush, eyeliner, lipliner, lip gloss, facial or body powder, sunscreens and blocks, nail polish, mousse, sprays, styling gels, nail conditioner, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, and rinses. Furthermore, the composition can be applied topically through the use of a patch or other delivery device. Delivery devices can include, but are not limited to, those that can be heated or cooled, as well as those that utilize iontophoresis or ultrasound.

Non-limiting examples of oral personal care compositions can include, without limitation, tablets, pills, capsules, drinks, beverages, powders, vitamins, supplements, health bars, candies, chews, and drops.

In another aspect, the present invention provides a personal care regimen comprising the use of at least one topical composition in combination with at least one oral composition. At least one of the compositions in this regimen comprises a dipeptide according to the present invention. Preferably, the regimen includes at least one topical composition comprising such dipeptide and at least one oral composition comprising such dipeptide.

In another aspect, the method comprises the step of injecting the dipeptide, preferably injecting the dipeptide into and/or under the skin. In a particular embodiment, the method comprises a treatment regimen comprising a combination of injection and/or oral administration and/or topical application of the dipeptide of the present invention.

II. Dipeptide

The compositions of the present invention comprise a dipeptide active. As used herein, the term "dipeptide" is broad enough to include one or more dipeptides, one or more derivatives of dipeptides, and combinations thereof. Preferably, the compositions comprise an effective amount, preferably a safe and effective amount, of such dipeptide.

A suitable peptide active for use herein is the dipeptide lys-thr and derivatives thereof. A preferred dipeptide derivative-containing composition is palmitoyl-lys-thr from Sederma, France. The use of threonine (Thr) as the C terminal residue in a dipeptide is particularly desirable, and can provide superior attributes in comparison to similar dipeptides terminating with a serine. For instance, the dipeptide Lys-Thr and N-acyl derivatives and esters, and nitrogen containing C terminal derivatives thereof can provide superior properties when compared to the corresponding Lys-Ser dipeptide.

Thus, the dipeptide of the present invention is a dipeptide where the C terminal amino acid is threonine ("Thr"). More preferably, the N terminal amino acid of such dipeptides is a basic amino acid, one which is positively charged at a pH of 6.0. These include the naturally occurring amino acids lysine (Lys), arginine (Arg) and histidine (His). Most preferred is the use of lysine. Thus, a particularly preferred dipeptide in accordance with the present invention has the sequence Lys-Thr and N-acyl derivatives and esters, and nitrogen containing C terminal derivatives thereof.

Dipeptides and derivatives in accordance with the present invention include, without limitation, His-Thr, Arg-Thr, Lys-Thr, Alk-His-Thr, Alk-Arg-Thr, Alk-Lys-Thr, His-Thr-OAlk, Arg-Thr-OAlk, Lys-Thr-OAlk, His-Thr-NR$_1$R$_2$, Arg-Thr-NR$_1$R$_2$, Lys-Thr-NR$_1$R$_2$, Alk-His-Thr-OAlk, Alk-Lys-Thr-NR$_1$R$_2$, Alk-Lys-Thr-OAlk. When used on the left side of the sequence, "Alk" refers to an N-acyl derivative as defined herein. When used on the right side of the sequence, "OAlk" refers to an ester group attached to the C terminal carbonyl of Thr (e.g., COOAlk). "NR$_1$R$_2$" is as defined herein.

In accordance with another aspect of the present invention, dipeptides of the present invention have the following structure:

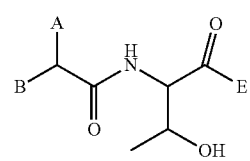

wherein
A=NH$_3^+$(CH$_2$)$_4$—,
NH$_2$=C(NH$_2$)NH—(CH$_2$)$_3$— or

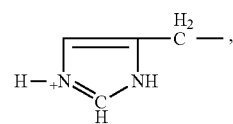

B=—NH$_2$, —NH$_3^+$, —NH-D,
D=an acyl group of 2-22 carbon atoms in length, or biotinyl and
E=—O-Alk, —NR$_1$R$_2$, —H, —O$^-$, or —OH,
wherein Alk is an alkyl group of 1-24 carbons in length, and R$_1$ and R$_2$ are independently H or an alkyl group of 1-12 carbons in length. In a particularly preferred embodiment, B=—NH-D. Note that the molecules of A (Lys, Arg and His respectively) are shown in their respective charged states at pH 6.0. It is understood that they may be present in an uncharged state as well and the representation of A above is meant to include both.

The dipeptides in accordance with the present invention, when provided in personal care compositions, are preferably provided in an amount which is safe and effective to treat at least one sign of an undesired keratinous tissue (e.g., skin, hair, or nail) condition. The phrase "to treat at least one undesired keratinous tissue (e.g., skin, hair, or nail) condition" as used herein means that the dipeptide provides an objectively measurable increase in its effect on some aspect of the keratinous tissue (e.g., skin, hair, or nail) condition when used topically and/or orally in an effective amount. This can be, for example, a greater reduction in wrinkles, increased potency, the ability to stimulate or inhibit at least one biochemical process within the skin, hair, or nails to a greater degree, and the like. Generally, this is determined based on comparison to a control.

The dipeptide is preferably included in an amount of from about $1 \times 10{-6}\%$ to about 10%, more preferably from about $1 \times 10{-6}\%$ to about 0.1%, and even more preferably from about $1 \times 10{-5}\%$ to about 0.01%, by weight of the personal care composition.

Reference to a "dipeptide" in accordance with the present invention means a dipeptide whose C terminal amino acid is Thr. These include, unless the context specifies otherwise, N-acyl derivatives thereof, as well as C terminal derivatives such as esters, acid halides, and nitrogen containing compounds as discussed herein.

The N-acyl derivatives are groups attached to the N terminal amino acid in place of a hydrogen and can include alkyl chains of carbon lengths of between 2 and 22 carbons. These can be linear or branched, substituted or unsubstituted, saturated or unsaturated, hydroxylated or not, containing sulfur or not. N-Acyl may also represent a biotinyl group. Similarly, the threonine may be in the form of a C terminal derivative including, for example, an acid, an ester with an alkyl chain having a carbon length of between 1 and 24 carbons ("Oalk"), preferably 1 to 3 carbons or 14 to 18 carbons. These can be linear or branched, substituted or unsubstituted, saturated or unsaturated, hydroxylated or not, containing sulfur or not. The C terminal derivative may also be NR1R2, in which R1 and R2 are independent of each other H or an alkyl chain of carbon length of between 1 and 12 carbons. These can be linear or branched, substituted or unsubstituted, saturated or unsaturated, hydroxylated or not, containing sulfur or not. Preferably, the acyl derivative attached to the N terminal amino acid is a palmitoyl group and most preferably, the C terminal amino acid is in the form of an acid.

All terms such as "skin aging", "signs of skin aging", and the like are used in the sense in which they are generally and widely used in the art of developing, testing and marketing personal care products. "Wrinkles" means furrows in the otherwise smooth surface of the facial skin, visible to the naked eye, generally in the average depth of 50 to more than 200 μm and essentially appearing with progressive age.

The term "amino acid" as employed herein includes and encompasses all of the naturally occurring and synthetic amino acids, either in the D- or L-configuration if optically active. The term "dipeptide" means a molecule comprising two amino acids as defined herein.

In order to enhance the bioavailability and cutaneous and/or epithelial barrier crossing of those peptides, their lipophilicity or lipophilic character can be increased either by acylation of the N-terminal $NH_2$ group of the peptide, by esterification of the carboxyl group with an alcohol, linear or branched, saturated or unsaturated, hydroxylated or not, or both.

In preferred methods of implementation of the invention, N-acyl groups used are lauroyl ($C_{12}$) or myristoyl ($C_{14}$) or palmitoyl ($C_{16}$) or stearoyl (Cis) or oleoyl ($C_{18:1}$) or arachidic ($C_{20}$) or linoleoyl ($C_{18:2}$). Biotinyl groups (biotin or derivatives) are also preferred. In a particularly preferred embodiment, the N terminal group is either H or Palmitoyl.

III. Optional Components/Ingredients

The compositions of the present invention can comprise one or more suitable desired optional components. For example, the composition can optionally include other active or inactive ingredients. Compositions comprising a peptide in combination with an optional keratinous tissue active, such as niacinamide, can be capable of providing additive and/or synergistic keratinous tissue (e.g., skin, hair, or nail) benefits.

For instance, such materials can be selected from the group consisting of sugar amines (e.g., N-acetylglucosamine), vitamin B3 compounds, sodium dehydroacetate, dehydroacetic acid and its salts, phytosterols, soy derivatives (e.g., equol and other isoflavones), niacinamide, phytantriol, farnesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole, their derivatives, and combinations thereof. Other examples of optional ingredients can include cationic polymers, conditioning agents (hydrocarbon oils, fatty esters, silicones), anti dandruff agents, antiseborrheic agents, antipsoriasis agents, suspending agents, viscosity modifiers, dyes, nonvolatile solvents or diluents (water soluble and insoluble), pearlescent aids, foam boosters, surfactants, nonionic cosurfactants, pediculocides, pH adjusting agents, perfumes, preservatives, chelants, chelating agents, proteins, UV absorbers, pigments, other amino acids, and other vitamins For instance, the compositions of the present invention may comprise one or more vitamins and/or amino acids such as: water soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their derivatives, water insoluble amino acids such as tyrosine, tryptamine, and their salts.

The compositions of the present invention may also contain one or more pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

Furthermore, the composition can comprise other peptides, such as those disclosed in U.S. Pat. No. 6,492,326, issued Dec. 10, 2002, to Robinson et al. (e.g., pentapeptides such as lys-thr-thr-lys-ser [SEQ ID NO: 1], and derivatives thereof).

Suitable pentapeptide derivatives include palmitoyl-lys-thr-thr-lys-ser [SEQ ID NO: 1], available from Sederma, France. Another optional dipeptide that can be used in the composition herein is carnosine. As used herein, the term "peptide" is broad enough to include one or more peptide, one or more peptide derivatives, and combinations thereof. In one embodiment, the optional ingredients do not comprise a peptide. In a particular embodiment, the optional ingredients comprise a peptide wherein said peptide is not a pentapeptide (e.g., palmitoyl-lys-thr-thr-lys-ser [SEQ ID NO: 1]). In another embodiment, the optional ingredients do not comprise the pentapeptide palmitoyl-lys-thr-thr-lys-ser [SEQ ID NO: 1]. In yet another embodiment, the optional ingredients comprise a peptide, such as a pentapeptide (e.g., palmitoyl-lys-thr-thr-lys-ser [SEQ ID NO: 1]) but said peptide is not present in an effective amount (e.g., it is included for a purpose other than the desired benefits disclosed herein) or such peptide is not present in a safe and effective amount.

Any other suitable optional component can also be included in the personal care composition of the present invention, such as those ingredients that are conventionally used in given product types. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g. hydroquinone, kojic acid, ascorbic acid, magnesiuim ascorbyl phosphate, ascorbyl glucoside, pyridoxine), enzymes, coenzymes, skin-conditioning agents (e.g. humectants and occlusive agents), skin soothing and/or healing agents and derivatives (e.g. panthenol, and derivatives such as ethyl panthenol, aloe vera, pantothenic acid and its derivatives, allantoin, bisabolol, and dipotassium glycyrrhizinate), skin treating agents (e.g. vitamin D compounds, mono-, di-, and tri-terpenoids, beta-ionol, cedrol), thickeners, and vitamins and derivatives thereof.

Several preferred optional components are discussed in more detail below.

1. Sugar Amines (Amino Sugars)

The compositions of the present invention can comprise a sugar amine, which is also known as amino sugar. Sugar amine compounds useful in the present invention can include those described in PCT Publication WO 02/076423 and U.S. Pat. No. 6,159,485.

In one embodiment, the composition comprises from about 0.01% to about 15%, more preferably from about 0.1% to about 10%, and even more preferably from about 0.5% to about 5% by weight of the composition, of sugar amine Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine 2. Vitamin B3 Compounds The compositions of the present invention can include a vitamin B3 compound. Vitamin B3 compounds are particularly useful for regulating skin conditions, as described in U.S. Pat. No. 5,939,082. In one embodiment, the composition comprises from about 0.001% to about 50%, more preferably from about 0.01% to about 20%, even more preferably from about 0.05% to about 10%, and still more preferably from about 0.1% to about 7%, even more preferably from about 0.5% to about 5%, by weight of the composition, of the vitamin B3 compound.

As used herein, "vitamin B3 compound" means a compound having the formula:

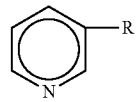

wherein R is —CONH$_2$ (i.e., niacinamide), —COOH (i.e., nicotinic acid) or —CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g., tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of $C_1$-$C_{22}$, preferably $C_1$-$C_{16}$, more preferably $C_1$-$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye, i.e., the ester is non-rubifacient). Non-vasodilating esters of nicotinic acid include tocopherol nicotinate and inositol hexanicotinate; tocopherol nicotinate is preferred.

Other derivatives of the vitamin B$_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1-C18). Specific examples of such derivatives include nicotinuric acid (C8H8N2O3) and nicotinyl hydroxamic acid (C6H6N2O2), which have the following chemical structures:

nicotinuric acid:

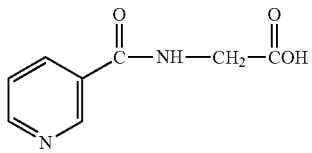

nicotinyl hydroxamic acid:

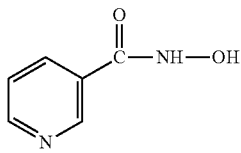

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin B3 compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin B3 compounds may be used herein. Preferred vitamin B3 compounds are niacinamide and tocopherol nicotinate. Niacinamide is more preferred.

When used, salts, derivatives, and salt derivatives of niacinamide are preferably those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate, preferably chloride), and organic carboxylic acid salts (including mono-, di- and tri-C1-C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan, for example, as described by W. Wenner, "The Reaction of L-Ascorbic and D-Iosascorbic Acid with Nicotinic Acid and Its Amide", J. Organic Chemistry, Vol. 14, 22-26 (1949). Wenner describes the synthesis of the ascorbic acid salt of niacinamide In a preferred embodiment, the ring nitrogen of the vitamin B3 compound is substantially chemically free (e.g., unbound and/or unhindered), or after delivery to the skin becomes substantially chemically free ("chemically free" is hereinafter alternatively referred to as "uncomplexed"). More preferably, the vitamin B3 compound is essentially uncomplexed. Therefore, if the composition contains the vitamin B3 compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin B3 compound is substantially uncomplexed in the composition prior to delivery to the keratinous tissue. Exemplary approaches to minimizing or preventing the formation of undesirable complexes include omission of materials which form substantially irreversible or other complexes with the vitamin B3 compound, pH adjustment, ionic strength adjustment, the use of surfactants, and formulating wherein the vitamin B3 compound and materials which complex therewith are in different phases. Such approaches are well within the level of ordinary skill in the art.

Thus, in a preferred embodiment, the vitamin B3 compound contains a limited amount of the salt form and is more preferably substantially free of salts of a vitamin B3 compound. Preferably the vitamin B3 compound contains less than about 50% of such salt, and is more preferably essentially free of the salt form. The vitamin B3 compound in the compositions hereof having a pH of from about 4 to about 7 typically contain less than about 50% of the salt form.

The vitamin B3 compound may be included as the substantially pure material, or as an extract obtained by suitable physical and/or chemical isolation from natural (e.g., plant) sources. The vitamin B3 compound is preferably substantially pure, more preferably essentially pure.

3. Dehydroacetic Acid (DHA)

The composition of this invention can include dehydroacetic acid, having the structure:

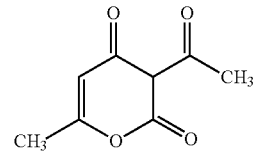

or pharmaceutically acceptable salts, derivatives or tautomers thereof. As used herein, "pharmaceutically acceptable" means that the salts of dehydroacetic acid are suitable for use in contact with the tissues of mammals to which they will be exposed without undue toxicity, incompatibility, instability, irritation, allergic response, and the like. The technical name for dehydroacetic acid is 3-Acetyl-6-methyl-2H-pyran-2,4 (3H)-dione and can be commercially purchased from Lonza.

Pharmaceutically acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium. Sodium, potassium, and ammonium salts of dehydroacetic acid are preferred. Highly preferred is sodium dehydroacetate which can be purchased from Tri-K, as Tristat SDHA.

Derivatives of dehydroacetic acid incude, but are not limited to, any compounds wherein the $CH_3$ groups are individually or in combination replaced by amides, esters, amino groups, alkyls, and alcohol esters. Tautomers of dehydroacetic acid are the isomers of dehydroacetic acid which can change into one another with great ease so that they ordinarily exist in equilibrium. Thus, tautomers of dehydroacetic acid can be described as having the chemical formula $C_8H_8O_4$ and generally having the structure above.

In one embodiment, the compositions of the present invention can comprise from about 0.001% to about 25% by weight of the composition, preferably from about 0.01% to about 10%, more preferably from about 0.05% to about 5%, and even more preferably from about 0.1% to about 1%, of dehydroacetic acid or pharmaceutically acceptable salts, derivatives or tautomers thereof.

4. Phytosterol

The compositions of the present invention can comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. More preferably, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company, and Cognis.

In one embodiment, the composition of the present invention comprises from about 0.0001% to about 25%, more preferably from about 0.001% to about 15%, even more preferably from about 0.01% to about 10%, still more preferably from about 0.1% to about 5%, and even more preferably from about 0.2% to about 2% phytosterol, by weight of the composition.

5. Salicylic Acid Compound

The compositions of the present invention may comprise a salicylic acid compound, its esters, its salts, or combinations thereof. In one embodiment of the compositions of the present invention, the salicylic acid compound preferably comprises from about 0.0001% to about 25%, more preferably from about 0.001% to about 15%, even more preferably from about 0.01% to about 10%, still more preferably from about 0.1% to about 5%, and even more preferably from about 0.2% to about 2%, by weight of the composition, of salicylic acid.

6. Hexamidine

The compositions of the present invention can include hexamidine compounds, its salts, and derivatives. Suitable hexamidine compounds useful in the present invention include those compositions that correspond to those of the following chemical structure:

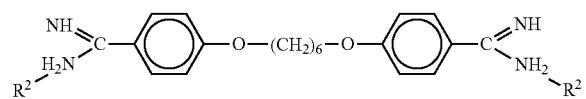

wherein $R^1$ and $R^2$ are organic acids (e.g., sulfonic acids, etc.).

In one embodiment, the hexamidine comprises from about 0.0001% to about 25%, more preferably from about 0.001% to about 10%, more preferably from about 0.01% to about 5%, and even more preferably from about 0.02% to about 2.5% by weight of the composition.

As used herein, hexamidine derivatives include any isomers and tautomers of hexamidine compounds including but not limited to organic acids and mineral acids, for example sulfonic acid, carboxylic acid, etc. Preferably, the hexamidine compounds include hexamidine diisethionate, commercially available as Eleastab® HP100 from Laboratoires Serobiologiques.

7. Dialkanoyl Hydroxyproline Compounds

The compositions of the present invention can comprise one or more dialkanoyl hydroxyproline compounds and their salts and derivatives. Suitable dialkanoyl hydroxyproline compounds of the present invention can include those corresponding to the following chemical structure:

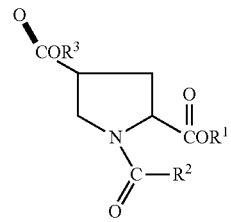

wherein $R^1$ is H, X, $C_1$-$C_{20}$ straight or branched alkyl,
X is metals (Na, K, Li, Mg, Ca) or amines (DEA, TEA);
$R^2$ is $C_1$-$C_{20}$ straight or branched alkyl;
$R^3$ is $C_1$-$C_{20}$ straight or branched alkyl.

In one embodiment, the dialkanoyl hydroxyproline compounds preferably comprise from about 0.01% to about 10%, more preferably from about 0.1% to about 5%, even more preferably from about 0.1% to about 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline.

8. Flavonoids

The compositions of the present invention can comprise a flavonoid compound. Flavonoids are broadly disclosed in U.S. Pat. Nos. 5,686,082 and 5,686,367. Examples of flavonoids particularly suitable for use in the present invention are one or more flavones, one or more isoflavones, one or more coumarins, one or more chromones, one or more dicoumarols, one or more chromanones, one or more chromanols, isomers (e.g., cis/trans isomers) thereof, and mixtures thereof.

Preferred for use herein are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Also preferred are favanones such as hesperitin, hesperidin, and mixtures thereof.

Flavonoid compounds useful herein are commercially available from a number of sources, e.g., Indofine Chemical Company, Inc., Steraloids, Inc., and Aldrich Chemical Company, Inc.

In one embodiment, the herein described flavonoid compounds comprise from about 0.01% to about 20%, more preferably from about 0.1% to about 10%, and even more preferably from about 0.5% to about 5%, by weight of the composition.

9. N-acyl Amino Acid Compound

The topical compositions of the present invention can comprise one or more N-acyl amino acid compounds. The amino acid can be one of any of the amino acids known in the art. The N-acyl amino acid compounds of the present invention can correspond to the formula:

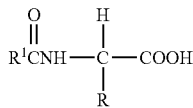

wherein R can be a hydrogen, alkyl (substituted or unsubstituted, branched or straight chain), or a combination of alkyl and aromatic groups. A list of possible side chains of amino acids known in the art are described in Stryer, *Biochemistry*, 1981, published by W.H. Freeman and Company. $R^1$ can be $C_1$ to $C_{30}$, saturated or unsaturated, straight or branched, substituted or unsubstituted alkyls; substituted or unsubstituted aromatic groups; or mixtures thereof.

Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof. N-acyl Phenylalanine corresponds to the following formula:

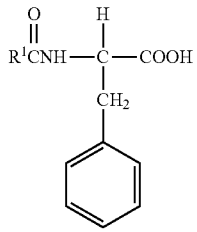

wherein $R^1$ can be $C_1$ to $C_{30}$, saturated or unsaturated, straight or branched, substituted or unsubstituted alkyls; substituted or unsubstituted aromatic groups; or mixtures thereof.

N-acyl Tyrosine corresponds to the following formula:

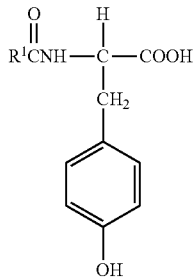

wherein $R^1$ can be $C_1$ to $C_{30}$, saturated or unsaturated, straight or branched, substituted or unsubstituted alkyls; substituted or unsubstituted aromatic groups; or mixtures thereof.

Particularly useful as a topical skin tone evening cosmetic agent is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

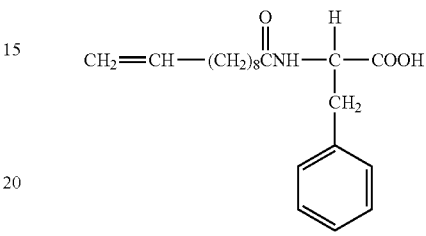

As used herein, N-undecylenoyl-L-phenylalanine is commercially available under the tradename Sepiwhite® from SEPPIC.

In one embodiment, of the present invention, the N-acyl amino acid preferably comprises from about 0.0001% to about 25%, more preferably from about 0.001% to about 10%, more preferably from about 0.01% to about 5%, and even more preferably from about 0.02% to about 2.5% by weight of the composition.

10. Retinoid

The compositions of this invention can comprise a retinoid, preferably in a safe and effective amount such that the resultant composition is safe and effective for regulating keratinous tissue condition, preferably for regulating visible and/or tactile discontinuities in keratinous tissue (e.g., regulating signs of skin aging). The compositions can comprise from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and Reissue 34,075, issued Sep. 22, 1992 to Purcell et al. Other suitable retinoids can include tocopheryl-retinoate [tocopherol ester of retinoic acid (transor cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids include retinol, retinyl palmitate, retinyl acetate, retinyl propionate, retinal and combinations thereof. More preferred is retinyl propionate, used most preferably from about 0.1% to about 0.3%.

11. Optional Peptide

The compositions of the present invention can comprise a peptide in addition to the peptide of the present invention. Suitable peptides can include, but are not limited to, di-, tri-, tetra-, penta-, and hexa-peptides and derivatives thereof. In one embodiment, the compositions comprise from about $1\times10^{-7}$% to about 20%, more preferably from about $1\times10^{-6}$% to about 10%, even more preferably from about $1\times10^{-5}$% to about 5%, by weight of optional peptide.

As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides. Preferred peptides contain at least one basic amino acid (e.g., histidine, lysine, arginine). More preferred peptides are the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg [SEQ ID NO:2], the pentapeptide lys-thr-thr-lys-ser [SEQ ID NO: 1], lipophilic derivatives of peptides, and metal complexes of the aforementioned (e.g., copper complex of the tripeptide his-gly-gly (also known as Iamin)) Other suitable peptides include Peptide CK (arg-lys-arg); Peptide CK+ (ac-arg-lys-arg-NH2); and Peptide E, arg-ser-arg-lys [SEQ ID NO:3]. A preferred commercially available tripeptide derivative-containing composition is Biopeptide CL®, which contains 100 ppm of palmitoyl-gly-his-lys and is commercially available from Sederma, France. A preferred commercially available pentapeptide derivative-containing composition is Matrixyl®, which contains 100 ppm of palmitoyl-lys-thr-thr-lys-ser [SEQ ID NO: 1] and is commercially available from Sederma, France.

Peptide derivatives useful herein include lipophilic derivatives, preferably palmitoyl derivatives. Preferably, the peptide is selected from palmitoyl-lys-thr-thr-lys-ser [SEQ ID NO: 1], palmitoyl-gly-his-lys, their derivatives, and combinations thereof.

12. Ascorbates and Other Vitamins

The compositions of the present invention may comprise one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate). Such vitamins can include, but are not limited to, vitamin B, vitamin B derivatives, vitamin K, vitamin K derivatives, vitamin D, vitamin D derivatives, vitamin E, vitamin E derivatives, and provitamins thereof, such as panthenol and mixtures thereof. In one embodiment, when vitamin compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the vitamin compound.

13. Particulate Material

The compositions of the present invention can comprise one or more particulate materials. Nonlimiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminun starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyerene microspheres such as for example those sold by Dyno Particles under the name Dynospheres, ethylene acrylate copolymer sold by Kobo under the name FloBead EA209, PTFE, polypropylene, aluminium starch ocetenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof. Especially preferred are spherical powders with an average primary particle size of from about 0.1 to about 75 microns, preferably from about 0.2 to about 30 microns.

Also useful herein are interference pigments. Interference pigments, for purposes of the present specification, are defined as thin platelike layered particles having two or more layers of controlled thickness with different refractive indices that yield a characteristic reflected color from the interference of typically two, but occasionally more, light reflections, from different layers of the platelike particle. The most common examples of interference pigments are micas layered with about 50-300 nm films of TiO2, Fe2O3, silica, tin oxide, and/or Cr2O3. Such pigments are often peralescent. Pearl pigments reflect, refract and transmit light because of the transparency of pigment particles and the large difference in the refractive index of mica platelets and, for example, the titanium dioxide coating. Useful intereference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls) and Eckart (e.g. Prestige Silk Red). Especially preferred are interference pigments with smaller particle sizes, with an average diameter of individual particles less than about 75 microns in the longest direction, preferably with an average diameter less than about 50 microns.

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2). Particularly preferred are charged dispersions of titanium dioxide, as are disclosed in U.S. Pat. No. 5,997,887.

Preferred colored or uncolored non-interference-type pigments have a primary average particle size of from about 10 nm to about 100,000 nm, more preferably from about 15 nm to about 5,000 nm, even more preferably from about 20 nm to about 1000 nm. Mixtures of the same or different pigment/powder having different particle sizes are also useful herein (e.g., incorporating a TiO2 having a primary particle size of from about 100 nm to about 400 nm with a TiO2 having a primary particle size of from about 10 nm to about 50 nm).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred. Particularly useful hydrophobic pigment treatments include polysiloxane treatments such as those disclosed in U.S. Pat. No. 5,143,722.

The composition of the present invention can include dispersed particles. In one embodiment, the composition can include at least 0.025% by weight of dispersed particles, more preferably at least 0.05%, still more preferably at least 0.1%, even more preferably at least 0.25%, and yet more preferably at least 0.5% by weight of the dispersed particles. In particular embodiments of the present invention, it is preferable to incorporate no more than about 20% by weight of dispersed particles, more preferably no more than about 10%, still more preferably no more than 5%, even more preferably no more than 3%, and yet more preferably no more than 2% by weight of dispersed particles.

14. Sunscreen Actives

The compositions of the subject invention may optionally contain a sunscreen active. As used herein, "sunscreen active" includes both sunscreen agents and physical sunblocks. Suitable sunscreen actives may be organic or inorganic.

A wide variety of conventional sunscreen actives are suitable for use herein. Sagarin, et al., at Chapter VIII, pages 189 et seq., of *Cosmetics Science and Technology* (1972), discloses numerous suitable actives. Particularly suitable sunscreen agents are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures of these compounds.

Preferred organic sunscreen actives useful in the compositions of the present invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, zinc oxide, titanium dioxide, and mixtures thereof. Especially preferred sunscreen actives include 4,4'-t-butylmethoxydibenzoylmethane, 2-ethylhexyl-p-methoxycinnamate, phenyl benzimidazole sulfonic acid, octocrylene, zinc oxide, and titanium dioxide, and mixtures thereof.

In one embodiment, the composition comprises from about 1% to about 20%, more typically from about 2% to about 10% by weight of the composition, of the sun screen active. Exact amounts will vary depending upon the sunscreen chosen and the desired Sun Protection Factor (SPF).

15. Anti-Cellulite Agents

The compositions of the present invention may also comprise an anti-cellulite agent. Suitable agents may include, but are not limited to, xanthine compounds (e.g., caffeine, theophylline, theobromine, and aminophylline In one embodiment, when anti-cellulite compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-cellulite compound.

16. Butylated Hydroxytoluene (BHT) and Butylated Hydroxyanisole (BHA)

The topical compositions of the present invention may comprise BHT or BHA.

For instance, BHT useful herein can be described by the general structure:

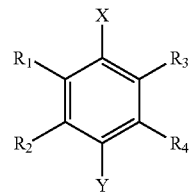

wherein X is OH or SH;

Y is selected from the group consisting of H, OH, OR$_5$, COOR$_5$, alkyl, cycloalkyl, heteroalkyl, heterocycloalkyl, aromatic, heteroaromatic, carboxamido, sulfonamido, carbamate, urea, and trialkylsilyl;

R$_1$, R$_2$, R$_3$, R$_4$ are selected from the group consisting of alkyl, cycloalkyl, heteroalkyl, heterocycloalkyl, aromatic, heteroaromatic, OR$_5$, carboxamido, sulfonamido, formyl, acyl, carboxyl, carboxylate, carbamate, urea, trialkylsilyl, hydroxyl, and hydrogen;

$R_5$ is selected from the group consisting of alkyl, cycloalkyl, heteroalkyl, heterocycloalkyl, aromatic, heteroaromatic, trialkylsilyl, acyl, and hydrogen.

In one embodiment, BHT and/or BHA comprises from about 0.0001% to about 20% by weight of the composition, more preferably from about 0.001% to about 10%, even more preferably from about 0.01% to about 5%, and still more preferably from about 0.1% to about 0.5%.

17. Desquamation Actives

A desquamation active may be added to the compositions of the present invention. In one embodiment, the composition comprises from about 0.01% to about 10%, preferably from about 0.1% to about 5%, more preferably from about 0.5% to about 2%, by weight of the composition, of a desquamation active. One desquamation system that is suitable for use herein comprises salicylic acid and zwitterionic surfactants and is described in U.S. Pat. No. 5,652,228. Another desquamation system that is suitable for use herein contains sulfhydryl compounds and zwitterionic surfactants and is described in U.S. Pat. No. 5,681,852, to Bissett. Zwitterionic surfactants such as those described in this referenced patent can also be useful as desquamatory agents herein, with cetyl betaine being particularly preferred.

18. Anti-Acne Actives

The compositions of the present invention can comprise one or more anti-acne actives. Examples of useful anti-acne actives include resorcinol, sulfur, erythromycin, and zinc. Further examples of suitable anti-acne actives are described in U.S. Pat. No. 5,607,980. In one embodiment, when anti-acne compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-acne compound.

19. Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include hydroxy acids (e.g., glycolic acid, lactic acid, lactobionic acid), keto acids (e.g., pyruvic acid), phytic acid, lysophosphatidic acid, stilbenes, cinnamates, resveratrol, kinetin, zeatin, dimethylaminoethanol, peptides from natural sources (e.g., soy peptides), and salts of sugar acids (e.g., Mn gluconate, Zn gluconate). In one embodiment, when anti-wrinkle/anti-atrophy compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-wrinkle/anti-atrophy compound.

20. Anti-Oxidants/Racial Scavengers

The compositions of the present invention can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as ascorbic acid (vitamin C), tocopherol (vitamin E), tocopherol sorbate, tocopherol acetate, other esters of tocopherol, 6-hydroxy-2,5,7,8-tetramethylchroman-2-carboxylic acid (commercially available under the tradename Trolox®), amines (e.g., N,N-diethylhydroxylamine, amino-guanidine), nordihydroguaiaretic acid, bioflavonoids, amino acids, silymarin, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, and grape skin/seed extracts may be used. Preferred anti-oxidants/radical scavengers can be selected from esters of tocopherol, more preferably tocopherol acetate.

In one embodiment, the composition comprises tocopherol sorbate. In one embodiment, the composition comprises from about 0.001% to about 20%, more preferably from about 0.01% to about 15%, even more preferably from about 0.1% to about 10%, still more preferably from about 0.5% to 5%, by weight of the composition, of the tocopherol sorbate.

As used herein, "tocopherol sorbate" refers to the sorbic acid ester of tocopherol, a detailed description of which can be found in issued U.S. Pat. No. 5,922,758 granted on Jul. 13, 1999 ("Methods and Compositions Employing 2,4-Dienoic Acid Esters of Tocopherols to Prevent or Reduce Skin Damage."

21. Conditioning Agents

The compositions of the present invention can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e g ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fucose), hyaluronic acid, lactamide monoethanolamine, acetamide monoethanolamine, panthenol, allantoin, and mixtures thereof. Also useful herein are the propoxylated glycerols described in U.S. Pat. No. 4,976,953.

Also useful are various $C_1$-$C_{30}$ monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

22. Chelators

The compositions of the present invention may also comprise a chelator or chelating agent. As used herein, "chelator" or "chelating agent" means an active agent capable of removing a metal ion from a system by forming a complex so that the metal ion cannot readily participate in or catalyze oxygen radical formation.

In one embodiment, a chelating agent is added to a composition of the present invention, preferably from about 0.1% to about 10%, more preferably from about 1% to about 5%, by weight of the composition. Exemplary chelators that are useful herein include those that are disclosed in U.S. Pat. No. 5,487,884. Preferred chelators useful in compositions of the subject invention include furildioxime and derivatives thereof. Also preferred is phytic acid.

23. Anti-Inflammatory Agents

An anti-inflammatory agent may be added to the compositions of the present invention. In one embodiment, an anti-inflammatory agent is added at a level of from about 0.01% to about 10%, preferably from about 0.5% to about 5%, by weight of the composition.

Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, salicylates, flufenamic acid, etofenamate, aspirin, and mixtures thereof.

Additional anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters).

24 Tanning Actives

The compositions of the present invention can comprise a tanning active. In one embodiment, the composition comprises from about 0.1% to about 20%, more preferably from about 2% to about 7%, and even more preferably from about 3% to about 6%, by weight of the composition, of a tanning active. A preferred tanning active is dihydroxyacetone.

25. Skin Lightening Agents

The compositions of the present invention can comprise a skin lightening agent. In one embodiment, the composition comprises from about 0.1% to about 10%, preferably from about 0.2% to about 5%, more preferably from about 0.5% to about 2%, by weight of the composition, of a skin lightening agent. Suitable skin lightening agents include those known in the art, including ascorbyl glucoside, kojic acid, arbutin, and tranexamic acid. Other skin lightening materials suitable for use herein can include Acitwhite (Cognis), Emblica® (Rona), Azeloglicina (Sinerga) and extracts (e.g. mulberry extract). A preferred skin lightening agent is ascorbyl glucoside.

26. Antimicrobial, Antibacterial and Antifungal Actives

The compositions of the present invention can comprise an antimicrobial or antifungal active. A safe and effective amount of an antimicrobial or antifungal active can be added to the present compositions. In one embodiment, the composition comprises from about 0.001% to about 10%, preferably from about 0.01% to about 5%, and more preferably from about 0.05% to about 2%, by weight of the composition, of an antimicrobial or antifungal active.

Preferred examples of actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neocycin sulfate, and mixtures thereof.

27. Thickening Agents (Including Thickeners and Gelling Agents)

The compositions of the present invention can comprise one or more thickening agents. In one embodiment, a thickening agent is present at a level of from about 0.05% to about 10%, preferably from about 0.1% to about 5%, and more preferably from about 0.25% to about 4%, by weight of the composition.

Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-30 alkyl acrylate crosspolymers and are commercially available as Carbopol® 1342, Carbopol® 1382, Pemulen TR-1, and Pemulen TR-2, from B.F. Goodrich. Examples of carboxylic acid polymer thickeners useful herein include those selected from the group consisting of carbomers, acrylates/C10-C30 alkyl acrylate crosspolymers, and mixtures thereof.

b. Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers include those described in U.S. Pat. Nos. 5,100,660; 4,849,484; 4,835,206; 4,628,078; 4,599,379; and EP 228,868.

c. Polyacrylamide Polymers

The compositions of the present invention can optionally comprise polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e. Gums

Other thickening and gelling agents useful herein include materials that are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

28. Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, when antiperspirant actives are present in the compositions of the instant invention, the compositions comprise from about 0.01% to about 50%, more preferably from about 0.1% to about 40%, and still more preferably from about 1% to about 30%, by weight of the composition, of the antiperspirant compound.

29. Detersive Surfactants

The compositions of the present invention can include detersive surfactant. The detersive surfactant component can be included to provide cleaning performance to the composition. The detersive surfactant component in turn can comprise anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, and generally can range from about 5% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions are the beta-alkyloxy alkane sulfonates. These surfactants conform to the formula

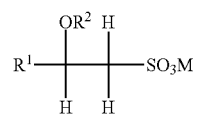

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

30. Cationic Polymers

The compositions of the present invention can comprise cationic polymer. When included, concentrations of the cationic polymer in the composition can typically range from about 0.05% to about 3%, preferably from about 0.075% to about 2.0%, more preferably from about 0.1% to about 1.0%. Preferred cationic polymers will have cationic charge densities of at least about 0.9 meq/gm, preferably at least about 1.2 meq/gm, more preferably at least about 1.5 meq/gm, but also preferably less than about 7 meq/gm, more preferably less than about 5 meq/gm, at the pH of intended use of the composition, which pH will generally range from about pH 3 to about pH 9, preferably between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, preferably between about 50,000 and about 5 million, more preferably between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula:

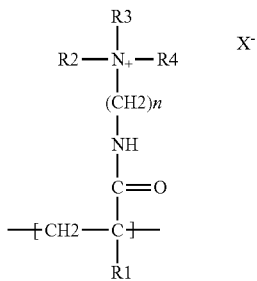

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula:

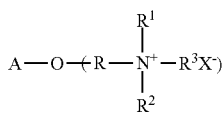

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

31. Nonionic Polymers

The compositions herein can comprise nonionic polymers. For instance, polyalkylene glycols having a molecular weight of more than about 1000 can be used. These can include those having the following general formula:

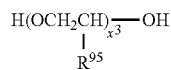

wherein $R^{95}$ is selected from the group consisting of H, methyl, and mixtures thereof. Preferred polyethylene glycol polymers can include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

32. Conditioning agents

Conditioning agents include any material which is used to give a particular conditioning benefit to keratinous tissue. For instance, in hair treatment compositions, suitable conditioning agents include those which deliver one or more benefits relating to shine, softness, compatibility, antistatic properties, wet-handling, damage, manageability, body, and greasiness. Conditioning agents useful in the compositions of the present invention can comprise a water insoluble, water dispersible, non-volatile liquid that forms emulsified, liquid particles. Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When included, the concentration of the conditioning agent in the composition can be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a number average particle diameter ranging from about 0.01 μm to about 50 μm. For small particle application to hair, the number average particle diameters typically range from about 0.01 μm to about 4 μm, preferably from about 0.01 μm to about 2 μm, more preferably from about 0.01 μm to about 0.5 μm. For larger particle application to hair, the number average particle diameters typically range from about 4 μm to about 50 μm, preferably from about 6 μm to about 30 μm, more preferably from about 9 μm to about 20 μm, more preferably from about 12 μm to about 18 μm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

b. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (M):

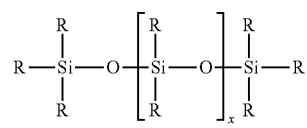

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

c. Amino and Cationic silicones

Cationic silicone fluids suitable for use in the compositions of the present invention include, but are not limited to, those which conform to the general formula (V):

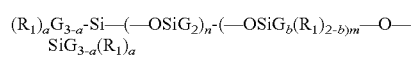

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 499; m is an integer from 1 to 2,000, preferably from 1 to 10; the sum of n and m is a number from 1 to 2,000, preferably from 50 to 500; $R_1$ is a monovalent radical conforming to the general formula $CqH_{2q}L$, wherein q is an integer having a value from 2 to 8 and L is selected from the following groups:

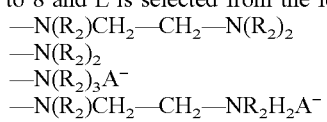

wherein $R_2$ is hydrogen, phenyl, benzyl, or a saturated hydrocarbon radical, preferably an alkyl radical from about $C_1$ to about C20, and $A^-$ is a halide ion.

An especially preferred cationic silicone corresponding to formula (V) is the polymer known as "trimethylsilylamodimethicone", which is shown below in formula (VI):

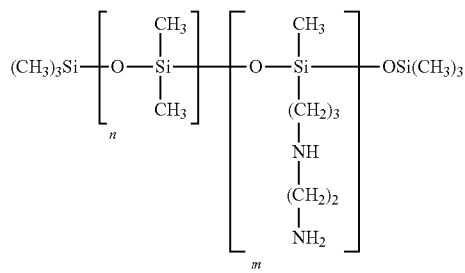

Other silicone cationic polymers which may be used in the compositions of the present invention are represented by the general formula (VII):

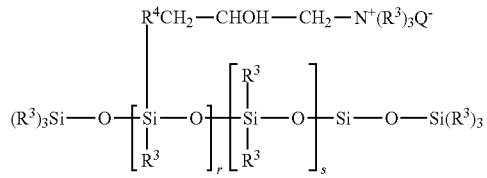

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE$^{56}$™, available from Union Carbide.

d. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

e. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

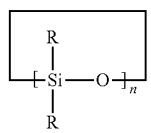

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1$NHR$^2$NH2 wherein each $R^1$ and $R^2$ independently is a $C_1$-$C_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

f. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

33. Organic Conditioning Oils

Compositions of the present invention may also comprise organic conditioning oil. In one embodiment, from about 0.05% to about 3%, preferably from about 0.08% to about 1.5%, more preferably from about 0.1% to about 1%, of at least one organic conditioning oil is included as a conditioning agent, either alone or in combination with other conditioning agents, such as the silicones (described herein).

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. The concentration of such hydrocarbon oils in the composition preferably range from about 0.05% to about 20%, more preferably from about 0.08% to about 1.5%, and even more preferably from about 0.1% to about 1%.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as Cm to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

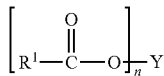

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

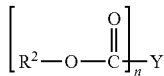

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

34. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

35. Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts.

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20μ, preferably up to about 5μ, more preferably up to about 2.5μ. Salts formed from other cations, such as sodium, may also be suitable. Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

36. Other Anti-Microbial Actives

The present invention can comprise one or more anti-fungal or anti-microbial actives. Suitable anti-microbial actives include coal tar, sulfur, whitfield's ointment, castellani's paint, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar. In one embodiment, one or more anti-fungal or anti-microbial active is combined with an anti-dandruff active selected from polyvalent metal salts of pyrithione.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein are ketoconazole and climbazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), preferably less than 10 μm. Selenium sulfide compounds are described, for example, in U.S. Pat. No. 2,694,668; U.S. Pat. No. 3,152,046; U.S. Pat. No. 4,089,945; and U.S. Pat. No. 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d. Keratolytic Agents

The present invention may further comprise one or more keratolytic agents such as Salicylic Acid.

e. Additional Anti-Microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

37. Humectant

The compositions of the present invention may contain a humectant. Humectants can be selected from the group consisting of polyhydric alcohols, water soluble alkoxylated nonionic polymers, and mixtures thereof. Humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

38. Suspending Agent

The compositions of the present invention may further comprise a suspending agent, preferably at concentrations effective for suspending water-insoluble material in dispersed form in the compositions or for modifying the viscosity of the composition. Such concentrations can preferably range from about 0.1% to about 10%, more preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine Still other suitable suspending agents include di(hydrogenated tallow)phthalic acid amide, and crosslinked maleic anhydride-methyl vinyl ether copolymer.

39. Terpene Alcohol

The compositions of the present invention may comprise a terpene alcohol or combinations of terpene alcohols. As used herein, "terpene alcohol" refers to organic compounds composed of two or more 5-carbon isoprene units [$CH_2=C(CH_3)$—$CH=CH_2$] with a terminal hydroxyl group. Preferably, the composition can comprise from about 0.001% to about 50%, preferably from about 0.01% to about 15%, more preferably from about 0.1% to about 10%, more preferably from about 0.5% to about 5%, still more preferably from about 1% to about 3%, by weight of the composition, of the terpene alcohol.

Examples of terpene alcohols that can be useful herein include farnesol, derivatives of farnesol, isomers of farnesol, geraniol, derivatives of geraniol, isomers of geraniol, phytantriol, derivatives of phytantriol, isomers of phytantriol, and mixtures thereof. A preferred terpene alcohol for use herein is farnesol.

a. Farnesol and Derivatives Thereof

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P. O. Box 14508, St. Louis, Mo.). A suitable derivative of farnesol is farnesyl acetate which is commercially available from Aldrich Chemical Company, P. O. Box 2060, Milwaukee, Wis.

b. Geraniol and Derivatives Thereof

Geraniol is the common name for the chemical known as 3,7-dimethyl-2,6-octadien-1-ol. As used herein, "geraniol" includes isomers and tautomers of such. Geraniol is commercially available from Aldrich Chemical Company (P. O. Box 2060, Milwaukee, Wis.). Suitable derivatives of geraniol include geranyl acetate, geranylgeraniol, geranyl pyrophosphate, and geranylgeranyl pyrophosphate, all of which are commercially available from Sigma Chemical Company, P. O. Box 14508, St. Louis, Mo. For example, geraniol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

c. Phytantriol and Derivatives Thereof

Phytantriol is the common name for the chemical known as 3,7,11,15, tetramethylhexadecane-1,2,3,-triol. Phytantriol is commercially available from BASF (1609 Biddle Avenue, Whyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

IV. Carrier

The compositions of the present invention can comprise an orally or a dermatologically acceptable carrier, or injectible liquid, depending upon the desired product form.

a. Dermatologically Acceptable Carrier

The topical compositions of the present invention can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition.

The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition. In one embodiment, oil-in-water emulsions are especially preferred.

Emulsions according to the present invention can contain an aqueous phase and a lipid or oil. Lipids and oils may be derived from animals, plants, or petroleum and may be natural or synthetic (i.e., man-made). Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form.

The compositions of the present invention can be in the form of pourable liquids (under ambient conditions). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Preferred water-in-silicone and oil-in-water emulsions are described in greater detail below.

A. Water-in-Silicone Emulsion

Water-in-silicone emulsions contain a continuous silicone phase and a dispersed aqueous phase.

(1) Continuous Silicone Phase

Preferred water-in-silicone emulsions of the present invention contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the retinoid. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in PCT Application WO 97/21423, published Jun. 19, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and still more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(2) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

(3) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

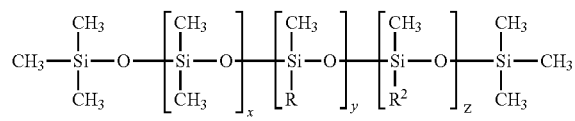

wherein R is C1-C30 straight, branched, or cyclic alkyl and $R^2$ is selected from the group consisting of $-(CH_2)_n-O-(CH_2CHR^3O)_m-H$, and $-(CH_2)_n-O-(CH_2CHR^3O)_m-(CH_2CHR^4O)_o-H$, wherein n is an integer from 3 to about 10; $R^3$ and $R^4$ are selected from the group consisting of H and C1-C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

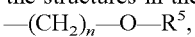

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries*, vol. 110, pp. 91-100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," *Provisional Communication, International Journal of Cosmetic Science*, 12, 135-139 (1990); and D. G. Krzysik et al., "A New Silicone Emulsifier For Water-in-Oil Systems," *Drug and Cosmetic Industry*, vol. 146(4) pp. 28-81 (April 1990).

Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

B. Oil-in-Water Emulsions

Other preferred topical carriers include oil-in-water emulsions, having a continuous aqueous phase and a hydrophobic, water-insoluble phase ("oil phase") dispersed therein.

Examples of suitable oil-in-water emulsion carriers are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(1) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

(2) Hydrophilic surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from non-ionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10-30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100. Nonlimiting examples of these alkylene oxide derived non-ionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: R$^1$ is H, C$_1$-C$_4$ alkyl, 2-hydroxyethyl, 2-hydroxypropyl, preferably C$_1$-C$_4$ alkyl, more preferably methyl or ethyl, most preferably methyl; R$^2$ is C$_5$-C$_{31}$ alkyl or alkenyl, preferably C$_7$-C$_{19}$ alkyl or alkenyl, more preferably C$_9$-C$_{17}$ alkyl or alkenyl, most preferably C$_{11}$-C$_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R$^2$CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C$_8$-C$_{24}$, more preferably C$_{10}$-C$_{20}$. The preferred fatty acid ester emulsifier is a blend of sorbitan or sorbitol C$_{16}$-C$_{20}$ fatty acid ester with sucrose C$_{10}$-C$_{16}$ fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. See, e.g., McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's, Detergents & Emulsifiers*, (North American edition 1979) M.C. Publishing Co.; and Schwartz, et al., *Surface Active Agents, Their Chemistry and Technology*, New York: Interscience Publishers, 1949. The cationic surfactants useful herein include cationic ammonium salts such as those having the formula:

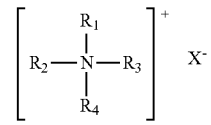

wherein R$_1$, is an alkyl group having from about 12 to about 30 carbon atoms, or an aromatic, aryl or alkaryl group having from about 12 to about 30 carbon atoms; R$_2$, R$_3$, and R$_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups of R$_1$, R$_2$, R$_3$, and R$_4$ can also contain ester and/or ether linkages, or hydroxy or amino group substituents (e.g., the alkyl groups can contain polyethylene glycol and polypropylene glycol moieties).

More preferably, R$_1$ is an alkyl group having from about 12 to about 22 carbon atoms; R$_2$ is selected from H or an alkyl group having from about 1 to about 22 carbon atoms; R$_3$ and R$_4$ are independently selected from H or an alkyl group having from about 1 to about 3 carbon atoms; and X is as described previously.

Still more preferably, R$_1$ is an alkyl group having from about 12 to about 22 carbon atoms; R$_2$, R$_3$, and R$_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH—(CH_2)_n$, wherein $R_5$ is an alkyl group having from about 12 to about 22 carbon atoms, and n is an integer from about 2 to about 6, more preferably from about 2 to about 4, and still more preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants can also be useful herein. See, e.g., U.S. Pat. No. 3,929,678, to Laughlin et al., issued Dec. 30, 1975. Nonlimiting examples of anionic surfactants include the alkoyl isethionates, and the alkyl and alkyl ether sulfates. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine Another suitable class of anionic surfactants are the water-soluble salts of the organic, sulfuric acid reaction products of the general formula:

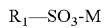

$$R_1—SO_3\text{-}M$$

wherein $R_1$ is chosen from the group including a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072; N-higher alkyl aspartic acids such as those produced according to the teaching of U.S. Pat. No. 2,438,091; and the products sold under the trade name "Miranol" and described in U.S. Pat. No. 2,528,378. Other examples of useful amphoterics include phosphates, such as coamidopropyl PG-dimonium chloride phosphate (commercially available as Monaquat PTC, from Mona Corp.).

Other amphoteric or zwitterionic surfactants useful herein include betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH$(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(3) Water

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology,* 2nd Edition, Vol. 1, pp. 32-43 (1972) contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80%, water; and the pentapeptide and/or pentapeptide derivative and the additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, *Cosmetics, Science and Technology,* 2nd Edition, Vol. 1, pp. 72-73 (1972), and/or an emollient. For example, an ointment may contain from about 2% to about 10% of an emollient; from about 0.1% to about 2% of a thickening agent; and the pentapeptide and/or pentapeptide derivative and the additional skin care active (or actives) in the above described amounts.

Compositions of this invention useful for cleansing ("cleansers") can be formulated with a suitable carrier, e.g., as described above, and preferably comprise from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, for exemplary surfactants useful herein. Examples of a broad variety of additional surfactants useful herein are described in *McCutcheon's Detergents and Emulsifiers,* North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in PCT Application, WO 96/33689, to Canter, et al., published on Oct. 31, 1996 and U.K. Patent, GB 2274585, issued on Aug. 3, 1994.

b. Orally Acceptable Carrier

The compositions of the present invention can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, powders, vitamins, supplements, health bars, candies, chews, and drops.

c. Injectible Liquid

The compositions of the present invention can also comprise a liquid that is acceptable for injection in and/or under the skin if the composition is to be injected. Any suitable acceptable liquid as known in the art or otherwise can be used.

V. Composition Preparation

The compositions useful for the methods of the present invention are generally prepared by conventional methods such as are known in the art of making topical and oral compositions and compositions for injection. Such methods typically can involve mixing of the ingredients in one or more steps to a relatively uniform state, with or without heating, cooling, application of vacuum, and the like.

VI. Methods for Treating Keratinous Tissue Condition

The compositions of the present invention can be useful for treating a number of mammalian keratinous tissue conditions. Such treatment of keratinous tissue conditions can include prophylactic and therapeutic regulation, including regulating the cosmetic appearance of the mammalian keratinous tissue. More specifically, such treatment methods can be directed to, but are not limited to, preventing, retarding, and/or treating uneven skin tone, reducing the size of pores in mammalian skin, regulating oily/shiny appearance of mammalian skin, thickening keratinous tissue (i.e., building the epidermis and/or dermis and/or subcutaneous layers of the skin and where applicable the keratinous layers of the nail and hair shaft), preventing, retarding, and/or treating uneven skin tone by acting as a lightening or pigmentation reduction cosmetic agent, preventing, retarding, and/or treating atrophy of mammalian skin, softening and/or smoothing lips, hair and nails of a mammal, preventing, retarding, and/or treating itch of mammalian skin, preventing, retarding, and/or treating the appearance of dark under-eye circles and/or puffy eyes, preventing, retarding, and/or treating sallowness of mammalian skin, preventing, retarding, and/or treating sagging (i.e., glycation) of mammalian skin, preventing and/or retarding tanning of mammalian skin, desquamating, exfoliating, and/or increasing turnover in mammalian skin, preventing, retarding, and/or treating hyperpigmentation such as post-inflammatory hyperpigmentation, preventing, retarding, and/or treating the appearance of spider vessels and/or red blotchiness on mammalian skin, preventing, retarding, and/or treating fine lines and wrinkles of mammalian skin, preventing, retarding, and/or treating skin dryness (i.e., roughness, scaling, flaking) and preventing, retarding, and/or treating the appearance of cellulite in mammalian skin. In a preferred embodiment, the composition is used to treat the signs of aging; in one aspect, the composition is used to regulate the signs of aging; in another aspect, the composition is used to reduce or decrease the signs of aging; in yet another aspect the composition is used to prevent the signs of aging in keratinous tissue (e.g., skin, hair, or nails).

For instance, the present invention can be useful for therapeutically regulating visible and/or tactile discontinuities in mammalian keratinous tissue, including discontinuities in skin texture and color. For example, the apparent diameter of pores can be decreased, the apparent height of tissue immediately proximate to pore openings can approach that of the interadnexal skin, the skin tone/color can become more uniform, and/or the length, depth, and/or other dimension of lines and/or wrinkles can be decreased.

Furthermore, compositions of the present invention can also be useful for cleansing (e.g., hair, body, facial), improving keratinous tissue feel (wet & dry) such as for hair (e.g., improving appearance/look, detangling, shine, gloss, decrease coefficient of friction, increase smoothness, color retention, decrease split ends, prevent hair breakage, prevent environmental damage such as sunlight damage, smoke damage, and damage from pollutants such as nitrogen oxides, sulfur oxides, ozone, and metals such as lead), odor control, oil control, conditioning, hair volume control, hair growth, and hair growth inhibition.

Regulating keratinous tissue conditions can involve topically applying to the keratinous tissue a safe and effective amount of a composition of the present invention. The amount of the composition that is applied, the frequency of application, and the period of use will vary widely depending upon the level of components of a given composition and the level of regulation desired, e.g., in view of the level of keratinous tissue damage present or expected to occur.

Furthermore, regulating keratinous tissue conditions can involve orally ingesting a safe and effective amount of a composition of the present invention. The amount of the composition that is ingested, the frequency of ingestion, and the period of use will vary widely depending upon the level of components of a given composition and the level of regulation desired, e.g., in view of the level of keratinous tissue damage present or expected to occur.

In one embodiment, the composition is chronically applied to the skin, e.g. topically. By "chronic application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic applications continue throughout the subject's lifetime. Typically applications would be on the order of about once per day over such extended periods, however, application rates can vary, and can include from about once per week up to about three times per day or more.

A wide range of quantities of the compositions of the present invention can be employed to provide a keratinous tissue appearance and/or feel benefit when applied topically. For example, quantities of the present compositions, which are typically applied per application are, in mg composition/ $cm^2$ keratinous tissue, from about 0.1 $mg/cm^2$ to about 20 $mg/cm^2$. A particularly useful application amount is about 0.5 $mg/cm^2$ to about 10 $mg/cm^2$.

Treating keratinous tissue condition can be practiced, for example, by applying a composition in the form of a skin lotion, clear lotion, milky lotion, cream, gel, foam, ointment, paste, emulsion, spray, conditioner, tonic, cosmetic, lipstick, foundation, nail polish, after-shave, or the like which is intended to be left on the skin or other keratinous tissue for some aesthetic, prophylactic, therapeutic or other benefit (i.e., a "leave-on" composition). After applying the composition to the keratinous tissue (e.g., skin), it is preferably left on for a period of at least about 15 minutes, more preferably at least about 30 minutes, even more preferably at least about 1 hour, even more preferably for at least several hours, e.g., up to about 12 hours. Any part of the external portion of the face, hair, and/or nails can be treated, (e.g., face, lips, under-eye area, eyelids, scalp, neck, torso, arms, hands, legs, feet, fingernails, toenails, scalp hair, eyelashes, eyebrows, etc.) The application of the present compositions may be done using the palms of the hands and/or fingers or a device or implement (e.g., a cotton ball, swab, pad, applicator pen, spray applicator, etc.)

Another approach to ensure a continuous exposure of the keratinous tissue to at least a minimum level of the composition is to apply the compound by use of a patch applied, e.g., to the face. Such an approach is particularly useful for problem skin areas needing more intensive treatment (e.g., facial crows feet area, frown lines, under eye area, upper lip, and the like). The patch can be occlusive, semi-occlusive or non-occlusive, and can be adhesive or non-adhesive. The composition can be contained within the patch or be applied to the skin prior to application of the patch. The patch can also include additional actives such as chemical initiators for exothermic reactions such as those described in PCT application WO 9701313, and in U.S. Pat. Nos. 5,821,250, 5,981,547, and 5,972,957 to Wu, et al. The patch can also contain a source of electrical energy (e.g., a battery) to, for example, increase delivery of the composition and active agents (e.g., iontophoresis). The patch is preferably left on the keratinous tissue for a period of at least about 5 minutes, more preferably at least about 15 minutes, more preferably still at least about 30 minutes, even more preferably at least about 1 hour, even more preferably at night as a form of night therapy.

In another embodiment, a personal care regimen is used to regulate the condition of keratinous tissue. By "regimen" is meant the use of an oral composition in conjunction with a topical composition. In a particular embodiment, the oral composition and the topical composition are packaged together as a kit. In another embodiment, the oral composition and the topical composition are not packaged together as a kit, but potential users of the regimen are informed (e.g. through advertisements, product labeling) that the oral and the topical compositions may be used in conjunction with one another to regulate the condition of kerationous tissue. At least one of the compositions, either oral or topical, comprises a dipeptide of the present invention. Preferably, both the oral and the topical compositions comprise a dipeptide of the present invention.

Examples

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Examples 1-5: Moisturizing Oil-in-Water Lotions/Creams

|  | 1 | 2 | 3 | 4 | 5 |
|---|---|---|---|---|---|
| Water Phase: | | | | | |
| Water | Qs | qs | qs | qs | qs |
| Glycerin | 3 | 5 | 7 | 10 | 15 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2 | 0.5 | — | 3 | 5 |
| Triethanolamine | — | 0.25 | — | — | — |
| D-panthenol | 0.5 | 0.1 | — | 0.5 | 1.5 |
| Sodium Dehydroacetate | 0.5 | 0.1 | 0.5 | 0.1 | 0.5 |
| Benzyl alcohol | 0.25 | 0.25 | 0.25 | 0.25 | 0.25 |
| GLW75CAP-MP (75% aq. TiO2 dispersion)[1] | — | 0.5 | 0.5 | — | — |
| Hexamidine diisethionate | — | 0.1 | — | — | — |
| Palmitoyl-dipeptide[2] | 0.00055 | 0.00055 | 0.0001 | 0.00055 | 0.00055 |
| N-acetyl glucosamine | 2 | 1 | 2 | 2 | 1 |
| Soy Isoflavone | 0.5 | — | — | — | — |
| Oil Phase: | | | | | |
| Salicylic Acid | — | — | 1.5 | — | — |
| Isohexadecane | 3 | 3 | 3 | 4 | 3 |

-continued

|  | 1 | 2 | 3 | 4 | 5 |
|---|---|---|---|---|---|
| PPG15 Stearyl Ether | — | — | 4 | — | — |
| Isopropyl Isostearate | 1 | 0.5 | 1.3 | 1.5 | 1.3 |
| Sucrose polyester | 0.7 | — | 0.7 | 1 | 0.7 |
| Dipalmitoylhydroxyproline | — | — | — | 1.0 | — |
| Undecylenoyl Phenylalanine | — | 0.5 | — | — | — |
| Phytosterol | — | — | 0.5 | — | 1.0 |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2 | 2.5 | 2 |
| Sodium acrylate/sodium acryloyldimethyl taurate copolymer/isohexadecane/polysorbate 80 | — | 3 | — | — | — |
| Additional Ingredients: | | | | | |
| Dimethicone/dimethiconol | — | 1 | 2 | 0.5 | 2 |
| Polymethylsilsequioxane | — | — | 0.25 | — | 1 |
| Nylon-12 | — | 0.5 | — | — | — |
| Prestige Silk Violet[3] | — | — | — | — | 1 |
| Timiron Splendid Red[4] | — | 1.0 | — | 2 | — |

[1]Available from Kobo products
[2]Palmitoyl-lysine-threonine available from Sederma
[3]Titanium dioxide coated mica violet interference pigment available from Eckart
[4]Silica and titanium dioxide coated mica red interference pigment available from Rona In a suitable vessel, combine the water phase ingredients and heat to 75° C. In a separate suitable vessel, combine the oil phase ingredients and heat to 75° C. Next, add the oil phase to the water phase and mill the resulting emulsion (e.g., with a Tekmar T-25). Then, add the thickener to the emulsion and cool the emulsion to 45° C. while stirring. At 45° C., add the remaining ingredients. Cool the product and stir to 30° C. and pour into suitable containers.

Examples 6-11: Moisturizing Silicone-in-Water Serums/Lotions

|  | 6 | 7 | 8 | 9 | 10 | 11 |
|---|---|---|---|---|---|---|
| Water Phase: | | | | | | |
| Water | Qs | Qs | qs | qs | qs | Qs |
| Glycerin | 3 | 5 | 7 | 10 | 15 | 10 |
| Disodium EDTA | 0.1 | 0.1 | 0.05 | 0.1 | 0.1 | 0.1 |
| Niacinamide | 2 | 0.5 | — | 3 | 5 | 3 |
| Sodium Dehydroacetate | 0.5 | 0.1 | — | 0.1 | 0.5 | 0.1 |
| D-panthenol | 0.5 | 0.1 | — | 0.5 | 1.5 | 0.5 |
| GLW75CAP-MP (75% aq. TiO2 dispersion)[1] | — | 0.4 | — | — | — | 0.4 |
| Ascorbyl Glucoside | — | — | — | — | — | 1 |
| Palmitoyl dipeptide[2] | 0.00055 | 0.00055 | 0.00055 | 0.00055 | 0.00055 | 0.00055 |
| Soy Isoflavone | — | 1 | — | — | — | — |
| N-acetyl glucosamine | 2 | — | 2 | — | 5 | — |
| Silicone/Oil Phase: | | | | | | |
| Cyclomethicone D5 | 10 | 5 | 5 | 10 | 7.5 | 10 |
| Dow Corning 9040 Silicone elastomer[3] | — | 10 | 5 | 5 | 7.5 | 5 |
| KS G-15AP silicone Elastomer[4] | 5 | — | 5 | 5 | 7.5 | 5 |
| Dimethione/dimethiconol | — | 2 | 2 | 1 | 2 | 1 |
| Dimethicone 50 csk | 1 | — | — | — | — | — |
| Salicylic Acid | — | — | 1.5 | — | — | — |
| Phytosterol | — | — | — | 1.0 | — | 0.1 |
| PPG-15 Stearyl Ether | — | — | 4 | 4 | — | — |
| Dehydroacetic acid | — | — | 0.5 | — | — | — |
| Undecylenoyl Phenylalanine | — | — | 0.5 | — | — | — |
| BHT | — | 0.5 | — | — | — | — |
| Vitamin E Acetate | — | 0.5 | 0.1 | 0.1 | — | 0.1 |

-continued

|  | 6 | 7 | 8 | 9 | 10 | 11 |
|---|---|---|---|---|---|---|
| Thickener: | | | | | | |
| Polyacrylamide/C1 3-14 isoparaffin/laureth-7 | 2.5 | 2.5 | — | — | — | 3 |
| Sodiumacrylate/sodium acryloyl dimethyl taurate copolymer/isohexadecane/ polysorbate 80 | — | — | — | 3 | — | — |
| Acrylates/C10-30 alkyl acrylates crosspolymer | — | — | 0.6 | — | 0.5 | — |
| Undecylenoyl Phenylalanine Premix | | | | | | |
| Undecylenoyl Phenylalanine | — | — | — | — | 1 | — |
| Water | — | — | — | — | 24 | — |
| Triethanolamine | — | — | — | — | 0.5 | — |
| Dipalmitoyl Hydroxy-Proline Premix: | | | | | | |
| Water | — | — | — | — | — | 4.4 |
| Triethanolamine | — | — | — | — | — | 0.1 |
| Dipalmitoylhyroxyproline | — | — | — | — | — | 1.0 |
| Additional Ingredients: | | | | | | |
| Triethanolamine | — | — | — | — | 0.6 | — |
| Polymethylsilsequioxane | 0.5 | 0.5 | 1.0 | 1 | 1 | 0.5 |
| Polyethylene | — | 0.5 | 0.5 | 1.0 | — | — |
| Flamenco Summit Green G30D[5] | — | — | 1.0 | — | — | — |
| Silca | — | — | 1 | 0.5 | — | — |
| Prestige Silk Red[6] | — | — | — | 1.0 | 1.0 | 1.0 |

[1]GLW75CAP-MP, 75% aqueous titanium dioxide dispersion from Kobo
[2]Palmitoyl-lysine-threonine available from Sederma
[3]A silicone elastomer dispersion from Dow Corning Corp
[4]A silicone elastomer dispersion from Shin Etsu,
[5]Titanium dioxide and tin oxide coated mica green interference pigment from Engelhard
[6]Titanium dioxide coated mica red interference pigment from Eckart In a suitable vessel, combine the water phase ingredients and mix until uniform. In a separate suitable container, combine the silicone/oil phase ingredients and mix until uniform. Separately, prepare the dipalmitoyl hydroxyproline premix and/or undecylenoyl phenylalanine premix by combining the premix ingredients in a suitable container, heat to about 70° C. while stirring, and cool to room temperature while stirring. Add half the thickener and then the silicone/oil phase to the water phase and mill the resulting emulsion (e.g., with a Tekmar T-25). Add the remainder of the thickener, the dipalmitoyl hydroxyproline premix and/or undecylenoyl phenylalanine premix, and then the remaining ingredients to the emulsion while stirring. Once the composition is uniform, pour the product into suitable containers.

Examples 12-17: Moisturizing Water-in-Silicone Creams/Lotions

| Component | 12 | 13 | 14 | 15 | 16 | 17 |
|---|---|---|---|---|---|---|
| Phase A | | | | | | |
| Water | qs | qs | qs | qs | qs | qs |
| Allantoin | 0.2 | 0.2 | 0.2 | 0.2 | 0.2 | 0.2 |
| disodium EDTA | 0.1 | 0.1 | 0.1 | 0.1 | 0.1 | 0.1 |
| ethyl paraben | 0.2 | 0.2 | 0.2 | 0.2 | 0.2 | 0.2 |
| propyl paraben | 0.1 | 0.1 | 0.1 | 0.1 | 0.1 | 0.1 |
| Caffeine | — | 1 | — | — | — | 1 |
| BHT | — | 0.1 | — | 0.015 | — | — |
| Dexpanthenol | 1 | 0.5 | 1 | 1 | 1 | 1 |
| Glycerin | 7.5 | 10 | 15 | 7.5 | 5 | 15 |
| hexamidine isethionate | — | — | 0.1 | 0.5 | — | — |
| Niacinamide | 2 | — | — | 2 | 3.5 | 5 |
| Palmitoyl-dipeptide[1] | 0.00055 | 0.00055 | 0.00055 | 0.00055 | 0.00055 | 0.00055 |
| Phenylbenzimidazole sulfonic acid | — | — | — | — | 1 | — |
| Sodium Dehydroacetate | 0.5 | — | — | 0.1 | 0.5 | 0.5 |
| benzyl alcohol | 0.25 | 0.25 | 0.25 | 0.25 | 0.25 | 0.25 |
| Triethanolamine | — | — | — | — | 0.6 | — |
| green tea extract | 1 | 1 | 1 | 1 | 1 | 1 |
| Soy Isoflavone | — | 0.5 | — | — | — | — |

| Component | 12 | 13 | 14 | 15 | 16 | 17 |
|---|---|---|---|---|---|---|
| N-acetyl glucosamine | 5 | — | 2 | 5 | 2 | — |
| sodium metabisulfite | 0.1 | 0.1 | 0.1 | 0.1 | 0.1 | 0.1 |
| Phase B | | | | | | |
| Cyclopentasiloxane | 15 | 15 | 18 | 15 | 15 | 18 |
| Titanium dioxide | 0.5 | 0.5 | 0.75 | 0.5 | 0.5 | 0.75 |
| Phase C | | | | | | |
| C12-C15 alkyl benzoate | — | — | — | 1.5 | 1.5 | — |
| vitamin E acetate | 0.5 | — | 1 | 0.5 | 0.5 | 1 |
| retinyl propionate | 0.3 | — | — | 0.2 | 0.2 | — |
| Undecylenoyl Phenylalanine | — | — | 0.5 | — | — | — |
| Dipalmitoyl hydroxyproline | — | 1 | — | — | — | — |
| Salicylic Acid | — | 1.5 | 1.5 | — | — | — |
| PPG-15 Stearyl Ether | 4 | 4 | 4 | — | — | — |
| Dehydroacetic Acid | — | 0.5 | 0.1 | — | — | — |
| Phytosterol | 1 | 0.5 | — | — | — | — |
| Phase D | | | | | | |
| KSG-21 silicone elastomer[2] | 4 | 4 | 5 | 4 | 4 | 5 |
| Dow Corning 9040 silicone elastomer[3] | 15 | 15 | 12 | 15 | 15 | 12 |
| Abil EM-97 Dimethicone Copolyol[4] | 0.5 | — | — | 0.5 | 0.5 | — |
| Polymethylsilsesquioxane | 2.5 | 2.5 | 2 | 2.5 | 2.5 | 2 |
| Undecylenoyl Phenylalanine Premix | | | | | | |
| Undecylenoyl Phenylalanine | — | — | — | — | 1 | — |
| Water | — | — | — | — | 24 | — |
| Triethanolamine | — | — | — | — | 0.5 | — |
| Phase E | | | | | | |
| Water | 8.8 | — | — | — | — | 8.85 |
| Triethanolamine | 0.2 | — | — | — | — | 0.25 |
| Dipalmitoylhyroxyproline | 0.5 | — | — | — | — | 1 |

[1]Palmitoyl-lysine-threonine available from Sederma
[2]KSG-21 is an emulsifying silicone elastomer available from Shin Etsu
[3]A silicon elastomer dispersion from Dow Corning Corp
[4]Abil EM-97 available from Goldschmidt Chemical Corporation In a suitable vessel, blend the Phase A components together with a suitable mixer (e.g., Tekmar model RW20DZM) and mix until all of the components are dissolved. Then, blend the Phase B components together in a suitable vessel and mill using a suitable mill (e.g., Tekmar RW-20) for about 5 minutes. Add the Phase C components to the Phase B mixture with mixing. Then, add the Phase D components to the mixture of Phases B and C and then mix the resulting combination of Phase B, C and D components using a suitable mixer (e.g., Tekmar RW-20) for about 1 hour. If applicable, prepare the undecylenoyl phenylalanine premix and/or Phase E by combining all ingredients, heating the ingredients to 70° C. while stirring, and cooling back to room temperature while stirring. Add the undecylenoyl phenylalanine premix and/or Phase E to Phase A while mixing. Next, slowly add Phase A to the mixture of Phases B, C and D with mixing. Mix the resulting mixture continually until the product is uniform. Mill the resulting product for about 5 minutes using an appropriate mill (e.g., Tekmar T-25).

Examples 18-22: Oil in Water Mousse

| | 18 | 19 | 20 | 21 | 22 |
|---|---|---|---|---|---|
| Water Phase: | | | | | |
| Water | Qs | qs | qs | qs | qs |
| Glycerin | 3 | 5 | 7 | 10 | 15 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2 | 0.5 | — | 3 | 5 |
| Triethanolamine | — | 0.25 | — | — | — |
| D-panthenol | 0.5 | 0.1 | — | 0.5 | 1.5 |
| Sodium Dehydroacetate | 0.5 | 0.1 | 0.5 | 0.1 | 0.5 |
| Benzyl alcohol | 0.25 | 0.25 | 0.25 | 0.25 | 0.25 |
| GLW75CAP-MP (75% aq. TiO2 dispersion)[1] | — | 0.5 | 0.5 | — | — |
| Undecylenoyl Phenylalanine | 1 | — | 0.5 | — | — |

-continued

|  | 18 | 19 | 20 | 21 | 22 |
|---|---|---|---|---|---|
| Hexamidine diisethionate | — | 0.1 | — | — | — |
| Palmitoyl-dipeptide[2] | 0.00055 | 0.00055 | 0.0001 | 0.00055 | 0.00055 |
| N-acetyl glucosamine | 2 | 1 | 2 | 2 | 1 |
| Soy Isoflavone | 0.5 | — | — | — | — |
| Oil Phase: | | | | | |
| Salicylic Acid | — | — | 1.5 | — | — |
| Isohexadecane | 3 | 3 | 3 | 4 | 3 |
| PPG15 Stearyl Ether | — | — | 4 | — | — |
| Isopropyl Isostearate | 1 | 0.5 | 1.3 | 1.5 | 1.3 |
| Sucrose polyester | 0.7 | — | 0.7 | 1 | 0.7 |
| Undecylenoyl Phenylalanine | — | 0.5 | — | — | — |
| Dipalmitoylhyroxyproline | — | — | — | 1.0 | — |
| Phytosterol | — | — | 0.5 | — | 1.0 |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2 | 2.5 | 2 |
| Sodium acrylate/sodium acryloyldimethyl taurate copolymer/isohexadecane/polysorbate 80 | — | 3 | — | — | — |
| Additional Ingredients: | | | | | |
| Dimethicone/dimethiconol | — | 1 | 2 | 0.5 | 2 |
| Polymethylsilsequioxane | — | — | 0.25 | — | 1 |
| Nylon-12 | — | 0.5 | — | — | — |
| Prestige Silk Violet[3] | — | — | — | — | 1 |
| Timiron Splendid Red[4] | — | 1.0 | — | 2 | — |
| Propellant Phase | | | | | |
| 152 A HFC Propellant | 3 | 4 | 2 | 3 | 2 |
| A-70 Propellant | 3 | 2 | 4 | 3 | 4 |

[1]Available from Kobo products
[2]Palmitoyl-lysine-threonine available from Sederma
[3]Titanium dioxide coated mica violet interference pigment available from Eckart
[4]Silica and titanium dioxide coated mica red interference pigment available from Rona In a suitable vessel, combine the water phase ingredients and heat to 75° C. In a separate suitable vessel, combine the oil phase ingredients and heat to 75° C. Next, add the oil phase to the water phase and mill the resulting emulsion (e.g., with a Tekmar T-25). Add the thickener to the emulsion and cool the emulsion to 45° C. while stirring. At 45° C., add the remaining ingredients. Cool the product with stirring to 30° C. and pour into suitable containers. Add propellant and product to a suitable aerosol container, and seal the container.

Examples 23-28: Silicone in Water Mousse

|  | 23 | 24 | 25 | 26 | 27 | 28 |
|---|---|---|---|---|---|---|
| Water Phase: | | | | | | |
| Water | Qs | Qs | qs | qs | qs | qs |
| Glycerin | 3 | 5 | 7 | 10 | 15 | 10 |
| Disodium EDTA | 0.1 | 0.1 | 0.05 | 0.1 | 0.1 | 0.1 |
| Niacinamide | 2 | 0.5 | — | 3 | 5 | 3 |
| Sodium Dehydroacetate | 0.5 | 0.1 | — | 0.1 | 0.5 | 0.1 |
| D-panthenol | 0.5 | 0.1 | — | 0.5 | 1.5 | 0.5 |
| GLW75CAP-MP (75% aq. TiO2 dispersion)[1] | — | 0.4 | — | — | — | 0.4 |
| Ascorbyl Glucoside | — | — | — | — | — | 1 |
| Palmitoyl dipeptide[2] | 0.00055 | 0.00055 | 0.00055 | 0.00055 | 0.00055 | 0.00055 |
| Soy Isoflavone | — | 1 | — | — | — | — |
| N-acetyl glucosamine | 2 | — | 2 | — | 5 | — |
| Silicone/Oil Phase: | | | | | | |
| Cyclomethicone D5 | 10 | 5 | 5 | 10 | 7.5 | 10 |
| Dow Corning 9040 silicone elastomer[3] | — | 10 | 5 | 5 | 7.5 | 5 |

|  | 23 | 24 | 25 | 26 | 27 | 28 |
|---|---|---|---|---|---|---|
| KS G-15AP silicone Elastomer[4] | 5 | — | 5 | 5 | 7.5 | 5 |
| Dimethione/Dimethiconol | — | 2 | 2 | 1 | 2 | 1 |
| Dimethicone 50 csk | 1 | — | — | — | — | — |
| Salicylic Acid | — | — | 1.5 | — | — | — |
| Phytosterol | — | — | — | 1.0 | — | 0.1 |
| PPG-15 Stearyl Ether | — | — | 4 | 4 | — | — |
| Dehydroacetic acid | — | — | 0.5 | — | — | — |
| Undecylenoyl Phenylalanine | — | — | 0.5 | — | — | — |
| BHT | — | 0.5 | — | — | — | — |
| Vitamin E Acetate | — | 0.5 | 0.1 | 0.1 | — | 0.1 |
| Thickener: | | | | | | |
| Polyacrylamide/C13-14 isoparaffin/laureth-7 | 2.5 | 2.5 | — | — | — | 3 |
| Sodiumacrylate/Sodium acryloyldimethyl taurate copolymer/isohexadecane/polysorbate 80 | — | — | — | 3 | — | — |
| Acrylates/C10-30 alkyl acrylates crosspolymer | — | — | 0.6 | — | 0.5 | — |
| Undecylenoyl Phenylalanine/Dipalmitoyl Hydroxyproline Premix | | | | | | |
| Undecylenoyl Phenylalanine | — | — | — | — | 1 | — |
| Water | — | — | — | — | 24 | 9 |
| Triethanolamine | — | — | — | — | 0.5 | 0.2 |
| Dipalmitoylhyroxyproline | — | — | — | — | — | 1.0 |
| Additional Ingredients: | | | | | | |
| Triethanolamine | — | — | — | — | 0.6 | — |
| Polymethyl Silsequioxane | 0.5 | 0.5 | 1.0 | 1 | 1 | 0.5 |
| Polyethylene | — | 0.5 | 0.5 | 1.0 | — | — |
| Flamenco Summit Green G30D[5] | — | — | 1.0 | — | — | — |
| Silica | — | — | 1 | 0.5 | — | — |
| Prestige Silk Red[6] | — | — | — | 1.0 | 1.0 | 1.0 |
| Propellant Phase | | | | | | |
| 152A HFCPropellant | 3 | 2 | 4 | 1 | 5 | 3 |
| A-70 Propellant | 3 | 4 | 2 | 5 | 1 | 3 |

[1]GLW75CAP-MP, 75% aqueous titanium dioxide dispersion from Kobo
[2]Palmitoyl-lysine-threonine available from Sederma
3A silicone elastomer dispersion from Dow Corning Corp
[4]A silicone elastomer dispersion from Shin Etsu,
[5]Titanium dioxide and tin oxide coated mica green interference pigment from Engelhard
[6]Titanium dioxide coated mica red interference pigment from Eckart In a suitable vessel, combine the water phase ingredients and mix until uniform. In a separate suitable container, combine the silicone/oil phase ingredients and mix until uniform. Separately, prepare the undecylenoyl phenylalanine and/or dipalmitoyl hydroxyproline premix by combining the premix ingredients in a suitable container, heat to about 70° C. while stirring, and cool to room temperature while stirring. Add half the thickener and then the silicone/oil phase to the water phase and mill the resulting emulsion (e.g., with a Tekmar T-25). Add the remainder of the thickener, the undecylenoyl phenylalanine and/or dipalmitoyl hydroxyproline premix, and then the remaining ingredients to the emulsion while stirring. Once the composition is uniform, pour the product into suitable containers. Add the product and propellant into an aerosol container. Seal the aerosol container.

Examples 29-34: Water Based Stick Formulations

|  | 29 | 30 | 31 | 32 | 33 | 34 |
|---|---|---|---|---|---|---|
| Water Phase: | | | | | | |
| Water | Qs | qs | qs | qs | qs | Qs |
| Palmitoyl dipeptide[1] | 0.00055 | 0.00055 | 0.00055 | 0.00055 | 0.00055 | 0.00055 |
| Propylene Glycol | 15 | 25 | 20 | 15 | 25 | 20 |
| Dipropylene Glycol | 50 | 40 | 45 | 50 | 40 | 45 |
| Sodium Stearate | 6 | 6 | 6 | 6 | 6 | 6 |
| Triethanolamine | 0.2 | 0.25 | — | 0.7 | 0.6 | — |
| N-Acetyl-D-Glucosamine | — | 2.0 | 0.5 | — | — | 2.0 |

| | 29 | 30 | 31 | 32 | 33 | 34 |
|---|---|---|---|---|---|---|
| Undecyenoyl Phenylalanine | — | 0.5 | — | 1 | — | — |
| Niacinamide | 2 | | 3.5 | | 2 | 3.5 |
| Sodium Dehydroacetate | 0.5 | 0.5 | 0.1 | 0.1 | 0.5 | 1.0 |
| Dipalmitoyl Hydroxyproline | 1 | — | — | 1 | 0.5 | — |

[1] Palmitoyl-lysine-threonine available from Sederma

All ingredients are combined into an appropriate size container, heated to 85° C., cooled and poured into stick containers at approximately 65° C.

Examples 35-40: Anhydrous Stick Formulations

| | 35 | 36 | 37 | 38 | 39 | 40 |
|---|---|---|---|---|---|---|
| Oil Phase: | | | | | | |
| Isopropyl Isostearate | 5 | 4 | 3 | 5 | 4 | 3 |
| Palmitoyl dipeptide[1] | 0.00055 | 0.00055 | 0.00055 | 0.00055 | 0.00055 | 0.00055 |
| Octylmethoxycinnamate | 5 | 2 | 2 | 5 | 2 | 2 |
| Cyclomethicone | Qs | qs | qs | qs | qs | qs |
| Phenyl trimethicone | 5 | 5 | 5 | 5 | 5 | 5 |
| Stearyl Alcohol | 15 | 17 | 15 | 15 | 17 | 15 |
| Behenyl Alcohol | 1 | 1 | 1 | 1 | 1 | 1 |
| Undecylenoyl Phenyl alanine | — | 0.5 | — | 1.0 | 0.5 | 0.5 |
| Dehydroacetic acid | 0.1 | 0.5 | 0.1 | 0.5 | 0.1 | 1.0 |
| Dipalmitoyl Hydroxyproline | 1 | — | 1.0 | — | 0.5 | — |
| Phytosterol | 1 | 0.5 | — | — | 0.5 | 1 |
| Salicylic Acid | — | — | 0.5 | 1.5 | — | 1.0 |

[1] Palmitoyl-lysine-threonine available from Sederma

All ingredients added to an appropriate size container, heated to 75° C. then cooled with stirring until mixture reaches approximately 45° C. The mixture is poured into stick containers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical personal care composition for treating skin, comprising:
   a. an effective amount of a dipeptide selected from the group consisting of His-Thr, Arg-Thr, Lys-Thr, Alk-His-Thr, Alk-Arg-Thr, Alk-Lys-Thr, His-Thr-OAlk, Arg-Thr-OAlk, Lys-Thr-OAlk, His-Thr-$NR_1R_2$, Arg-Thr-$NR_1R_2$, Lys-Thr-$NR_1R_2$, Alk-His-Thr-OAlk, Alk-Lys-Thr-$NR_1R_2$, Alk-Lys-Thr-OAlk, wherein Alk is an N-acyl group of 2 to 22 carbon atoms in length, OAlk is an ester group of 1 to 24 carbons in length, and $R_1$ and $R_2$ are, independently, hydrogen or an alkyl group of 1 to 12 carbons in length; and
   b. a dermatologically acceptable carrier.

2. The composition of claim 1, further comprising an additional active ingredient selected from the group consisting of niacinamide, N-acetylglucosamine, sodium dehydroacetate, phytosterols, soy derivatives, hexamidines, retinoids, water soluble vitamins, water insoluble vitamins, sunscreen actives, butylated hydroxytoluene, butylated hydroxyanisole, pentapeptides, and combinations thereof.

3. The composition of claim 2, wherein the additional active comprises retinyl propionate.

4. The composition of claim 1, further comprising an optional ingredient selected from N-acyl phenylalanine, palmitoyl-lys-thr-thr-lys-ser (palmitoyl-SEQ ID NO: 1), or a combination of these.

5. The composition of claim 1, further comprising from 0.01% to 20% of a particulate material.

6. The composition of claim 5, wherein the particulate material comprises a spherical powder with an average primary particle size of 0.1 to 75 microns.

7. The composition of claim 6, wherein the particulate material comprises a modified starch, silicone polymer, or combination of these.

8. The composition of claim 5, wherein the particulate material comprises titanium dioxide.

9. The composition of claim 1, further comprising a non-volatile silicone fluid.

10. The composition of claim 9, wherein the non-volatile silicone fluid comprises dimethicone.

11. A topical personal care composition for treating hair, comprising:
    a. an effective amount of a dipeptide selected from the group consisting of His-Thr, Arg-Thr, Lys-Thr, Alk-His-Thr, Alk-Arg-Thr, Alk-Lys-Thr, His-Thr-OAlk, Arg-Thr-OAlk, Lys-Thr-OAlk, His-Thr-$NR_1R_2$, Arg-Thr-$NR_1R_2$, Lys-Thr-$NR_1R_2$, Alk-His-Thr-OAlk, Alk-Lys-Thr-$NR_1R_2$, Alk-Lys-Thr-OAlk, wherein Alk is an N-acyl group of 2 to 22 carbon atoms in length, OAlk is an ester group of 1 to 24 carbons in length, and $R_1$ and $R_2$ are, independently, hydrogen or an alkyl group of 1 to 12 carbons in length; and
    b. a dermatologically acceptable carrier.

12. The composition of claim 11, further comprising from 0.01% to 10% of a silicone conditioning agent.

13. The composition of claim 11, further comprising from 0.1% to 4% of an anti-dandruff active.

14. The composition of claim 11, further comprising a detersive surfactant.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Lys Thr Thr Lys Ser
```

```
1                        5

<210> SEQ ID NO 2
<211> LENGTH: 4
<212> TYPE: PRT
<213> ORGANISM: Artificial Sequence
<220> FEATURE:
<223> OTHER INFORMATION: Synthetic sequence

<400> SEQUENCE: 2

Gly Gln Pro Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic sequence

<400> SEQUENCE: 3

Arg Ser Arg Lys
1
```